(12) United States Patent
Kanaki

(10) Patent No.: US 11,530,387 B2
(45) Date of Patent: Dec. 20, 2022

(54) METHOD FOR INDUCING DIFFERENTIATION INTO AND PRODUCING BEIGE AND WHITE ADIPOCYTES

(71) Applicant: NISSAN CHEMICAL CORPORATION, Tokyo (JP)

(72) Inventor: Tatsuro Kanaki, Shiraoka (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 134 days.

(21) Appl. No.: 16/764,381

(22) PCT Filed: Nov. 16, 2018

(86) PCT No.: PCT/JP2018/042388
§ 371 (c)(1),
(2) Date: May 14, 2020

(87) PCT Pub. No.: WO2019/098310
PCT Pub. Date: May 23, 2019

(65) Prior Publication Data
US 2020/0277575 A1 Sep. 3, 2020

(30) Foreign Application Priority Data
Nov. 16, 2017 (JP) .............................. JP2017-221360

(51) Int. Cl.
*C12N 5/077* (2010.01)

(52) U.S. Cl.
CPC ........ *C12N 5/0653* (2013.01); *C12N 2501/33* (2013.01); *C12N 2501/39* (2013.01); *C12N 2501/999* (2013.01); *C12N 2506/1384* (2013.01); *C12N 2533/70* (2013.01)

(58) Field of Classification Search
CPC .............. C12N 5/0653; C12N 2501/33; C12N 2501/39; C12N 2506/1384; C12N 2533/70; C12N 2501/999
See application file for complete search history.

(56) References Cited

U.S. PATENT DOCUMENTS

| 6,153,432 A | 11/2000 | Halvorsen et al. |
| 6,322,784 B1 | 11/2001 | Pittenger et al. |
| 9,422,522 B2 * | 8/2016 | Bhasin ...................... A61P 3/10 |
| 2014/0106248 A1 | 4/2014 | Luo et al. |
| 2014/0106348 A1 * | 4/2014 | Nishino ............. G01N 33/5044 435/6.11 |
| 2016/0060601 A1 | 3/2016 | Nishino et al. |
| 2019/0071635 A1 | 3/2019 | Hayashi et al. |

FOREIGN PATENT DOCUMENTS

| EP | 2878664 A1 | 6/2015 | |
| EP | 3252151 A1 | 12/2017 | |
| JP | 2006-254832 A | 9/2006 | |
| WO | WO 2007/004469 A1 | 1/2007 | |
| WO | WO-2007004469 A1 * | 1/2007 | ......... G01N 33/5044 |
| WO | WO 2014/017513 A1 | 1/2014 | |
| WO | WO 2016/121896 A1 | 8/2016 | |
| WO | WO 2016/125884 A1 | 8/2016 | |
| WO | WO 2017/057599 A1 | 4/2017 | |
| WO | WO 2017/154952 A1 | 9/2017 | |

OTHER PUBLICATIONS

Wang et al., Characterization and evaluation of the differentiation ability of human adipose-derived stem cells growing in scaffold-free suspension culture. Cytotherapy, vol. 16 (2014) pp. 485-495. (Year: 2014).*
Wang et al., "Characterization and evaluation of the differentiation ability of human adipose-derived stem cells growing in scaffold-free suspension culture," *Cyotherapy*, 16(4): 485-495 (2014).
Japanese Patent Office, International Search Report in International Patent Application No. PCT/JP2018/042388 (dated Feb. 19, 2019).
Welter et al., "Assessing Adipogenic Potential of Mesenchymal Stem Cells: A Rapid Three-Dimensional Culture Screening Technique," *Stem Cells International*, 2013:806525 (2013).

* cited by examiner

*Primary Examiner* — Kara D Johnson
(74) *Attorney, Agent, or Firm* — Leydig, Voit & Mayer, Ltd.

(57) ABSTRACT

The present invention provides a method for producing a unilocular adipocyte including inducing differentiation into unilocular adipocytes of mesenchymal cells having differentiation potency into adipocytes by culturing the mesenchymal cells in suspension in a liquid medium composition capable of culturing cells or tissues in suspension, wherein the liquid medium composition contains a polymer compound having an anionic functional group that binds via a divalent metal cation to form a structure capable of suspending cells or tissues, and the method wherein the polymer compound is polysaccharide, preferably polysaccharide containing a glucuronic acid moiety, more preferably deacylated gellan gum, diutan gum or xanthan gum or a salt thereof.

10 Claims, 3 Drawing Sheets

TOYOBO differentiation medium | IDI differentiation medium (10% FBS)

TOYOBO differentiation medium

METHOD FOR INDUCING DIFFERENTIATION INTO AND PRODUCING BEIGE AND WHITE ADIPOCYTES

CROSS-REFERENCE TO RELATED APPLICATIONS

This patent application is the U.S. national phase of International Patent Application No. PCT/JP2018/042388, filed on Nov. 16, 2018, which claims the benefit of Japanese Patent Application No. 2017-221360, filed on Nov. 16, 2017, which are incorporated by reference in their entireties herein.

TECHNICAL FIELD

The present invention relates to a method for inducing differentiation of mesenchymal cells into white adipocytes and beige adipocytes and the like.

BACKGROUND ART

In recent years, in the field of life sciences, research of culturing pluripotent stem cells such as iPS cells and ES cells, mesenchymal stem cells and the like to induce differentiation into organ cells of interest and transplanting the obtained cells has been actively performed. Transplantation of adipocytes has also been studied. Transplantation of adipocytes has been studied in various ways, such as breast re-formation after breast cancer treatment, reduction of wrinkles for beauty care, and the like. Recently, studies have also begun on a method for incorporating a gene vector capable of producing a normal gene product into a precursor-adipocyte and transplanting same to gene mutated patients as a gene therapy. As the background, there are advantages that the transplantation of adipocytes is less likely to cause cancer because the adipocytes themselves have low proliferation potential as compared to pluripotent stem cells such as iPS cell, ES cell and the like, and transplantation surgery is easily performed since adipocytes are transplanted subcutaneously. Therefore, the hurdle for adipocyte transplantation is considered to be lower than that for other cell therapies.

On the other hand, it has been drawing attention from the recent studies that adipocytes not only contain a large amount of lipids such as triglyceride and the like but also have a role as an endocrine organ important for the body. For example, leptin that suppresses appetite, adiponectin that has an anti-diabetic action, TNF-alpha that controls inflammation and the like can be recited as examples of factors secreted by adipocytes. Therefore, adipocytes are often used for researches on metabolic syndrome, drug discovery studies for diabetes and lipids, development of health foods and the like. Recently, the studies of not only white adipocytes that store lipids, but also beige adipocytes that efficiently convert excess nutrients in the body into heat by production of heat by the adipocytes themselves are attracting attention. Beige adipocytes are considered to exist in the body due to changes from white adipocytes or differentiation from pre-cursors-adipocyte. Researches on the beige adipocytes have recently been receiving particular attention, and researches on medicaments and health foods that promote induction of differentiation into beige adipocytes have been actively performed. Furthermore, attempts have been studied to treat metabolic diseases such as diabetes and obesity by industrially producing the beige adipocytes and using same for transplantation treatments.

In such a case, adipocytes that have been experimentally used so far have been produced by a method including culturing human adipocyte precursors and 3T3-L1 cells in a monolayer in a petri dish or a plate, changing the medium to a differentiation induction medium, and further culturing the cells to cause differentiation into adipocyte-like cells. The cells differentiated by this method are in a state of being attached to a petri dish or a plate and show a spindle-like shape. They also show a multilocular morphology in which many small lipid droplets accumulate in the cells. On the other hand, the adipocytes separated from the body have a spherical shape, are unilocular containing one large lipid droplet in single cell, and have the property of floating in a medium. Therefore, adipocytes differentiated in vitro and adipocytes derived from the body are clearly different in various points, which form a major obstacle to the development of the above-mentioned researches.

Furthermore, this limitation in monolayer culture inhibits not only the preparation of white adipocytes like those in the body but also the preparation, research and production of beige adipocytes.

The present inventors have successfully developed a medium composition capable of culturing cells and tissues while keeping the suspended state, without substantially increasing the viscosity of the liquid medium (patent documents 1, 2). In addition, a production method of erythrocytes using the medium composition (patent document 3), a culture method of vascular smooth muscle cells (patent document 4), a method of producing tumor-bearing mammalian model (patent document 5), a method of coculturing cancer cells and cells surrounding the cancer cells (patent document 6) and the like have been reported. Furthermore, a medium composition with improved cell recovery has been reported (patent document 7).

DOCUMENT LIST

Patent Documents

[patent document 1] WO 2014/017513
[patent document 2] US-A-2014/0106348
[patent document 3] US-A-2016/0060601
[patent document 4] WO 2016/121896
[patent document 5] WO 2016/125884
[patent document 6] WO 2017/057599
[patent document 7] WO 2017/154952

SUMMARY OF THE INVENTION

Problems to be Solved by the Invention

The present invention aims to provide a method for inducing in vitro differentiation of white adipocytes having a phenotype similar to that of adipocytes separated from a body. The present invention also aims to provide a method for inducing in vitro differentiation of beige adipocytes.

Means of Solving the Problems

The present inventors have conducted intensive studies in an attempt to solve the aforementioned problems and found that suspension culture of mesenchymal cells having differentiation potency into adipocytes such as precursor-adipocyte, mesenchymal stem cell and the like in an adipocyte differentiation induction medium containing a polymer compound having an anionic functional group that binds via a divalent metal cation to form a structure capable of suspending cells or tissues results in differentiation of the mesenchymal cells into spherical unilocular adipocytes (white adipocytes) having one large lipid droplet in one cell, like the adipocytes separated from the body. Since these adipocytes are intracellular lipid droplets and suspended spontaneously in the medium, the floating white adipocytes could be easily isolated by gradually decreasing the concentration of the deacylated gellan gum. When the white adipocytes were further cultured for a long period, the expression of the beige adipocyte marker UCP-1 that controls energy consumption by promoting heat production was enhanced, and beige adipocyte-like phenotype was exhibited. Based on the above-mentioned findings, the present inventors conducted further studies and completed the present invention.

That is, the present invention relates to the following.

[1] A method for producing a unilocular adipocyte comprising inducing differentiation into unilocular adipocytes of mesenchymal cells having differentiation potency into adipocytes by culturing the mesenchymal cells in suspension in a liquid medium composition capable of culturing cells or tissues in suspension, wherein the liquid medium composition comprises a polymer compound having an anionic functional group that binds via a divalent metal cation to form a structure capable of suspending cells or tissues.

[2] The method of [1], wherein the mesenchymal cell is a precursor-adipocyte, a mesenchymal stem cell, or a fibroblast.

[3] The method of [1] or [2], wherein the polymer compound is a polysaccharide.

[4] The method of [3], wherein the polysaccharide comprises a glucuronic acid moiety.

[5] The method of [4], wherein the polysaccharide is deacylated gellan gum, diutan gum, or xanthan gum, or a salt thereof.

[6] The method of [5], wherein the polysaccharide is deacylated gellan gum or a salt thereof, and a concentration of the deacylated gellan gum or a salt thereof in the medium composition is 0.01 to 0.05% (w/v).

[7] The method of [5], wherein the polysaccharide is diutan gum or xanthan gum or a salt thereof, and a concentration of the diutan gum or xanthan gum or a salt thereof in the medium composition is 0.01 to 0.5% (w/v).

[8] The method of any of [1] to [7], wherein the medium composition comprises a divalent metal cation.

[9] The method of [8], wherein the divalent metal cation is a calcium ion.

[10] The method of any of [1] to [9], wherein the medium composition comprises an adipocyte differentiation-inducing factor.

[11] The method of [10], wherein the adipocyte differentiation-inducing factor is at least one factor selected from the group consisting of insulin, glucocorticoid receptor agonist, cAMP phosphodiesterase inhibitor, cyclooxygenase inhibitor, prostaglandin, long chain fatty acid, triiodothyronine, and PPARγ agonist.

[12] The method of [11], wherein the adipocyte differentiation-inducing factor contains insulin, a glucocorticoid receptor agonist, and a cyclooxygenase inhibitor.

[13] The method of [12], wherein the glucocorticoid receptor agonist is dexamethasone.

[14] The method of [12] or [13], wherein the cyclooxygenase inhibitor is indomethacin.

[15] The method of [11], wherein the adipocyte differentiation-inducing factor contains insulin, a glucocorticoid receptor agonist, and a cAMP phosphodiesterase inhibitor.

[16] The method of [15], wherein the glucocorticoid receptor agonist is dexamethasone.

[17] The method of [15] or [16], wherein the cAMP phosphodiesterase inhibitor is 3-isobutyl-1-methylxanthine.

[18] The method of any one of [1] to [17], wherein the unilocular adipocyte is UCP-1-positive.

[19] The method of any one of [1] to [18], further comprising lowering a concentration of the polymer compound in the cell suspension obtained by the suspension culture to a concentration not allowing suspending of the mesenchymal cells, and collecting unilocular adipocytes that maintain the floating state.

Effect of the Invention

According to the present invention, a unilocular white adipocyte containing one large fat droplet in one cell can be produced in vitro like adipocytes separated from a body. According to the present invention, moreover, a beige-like adipocyte expected to be applicable to not only drug discovery studies but also treatments of diabetes and obesity by transplantation can be produced in vitro.

Figure 1:
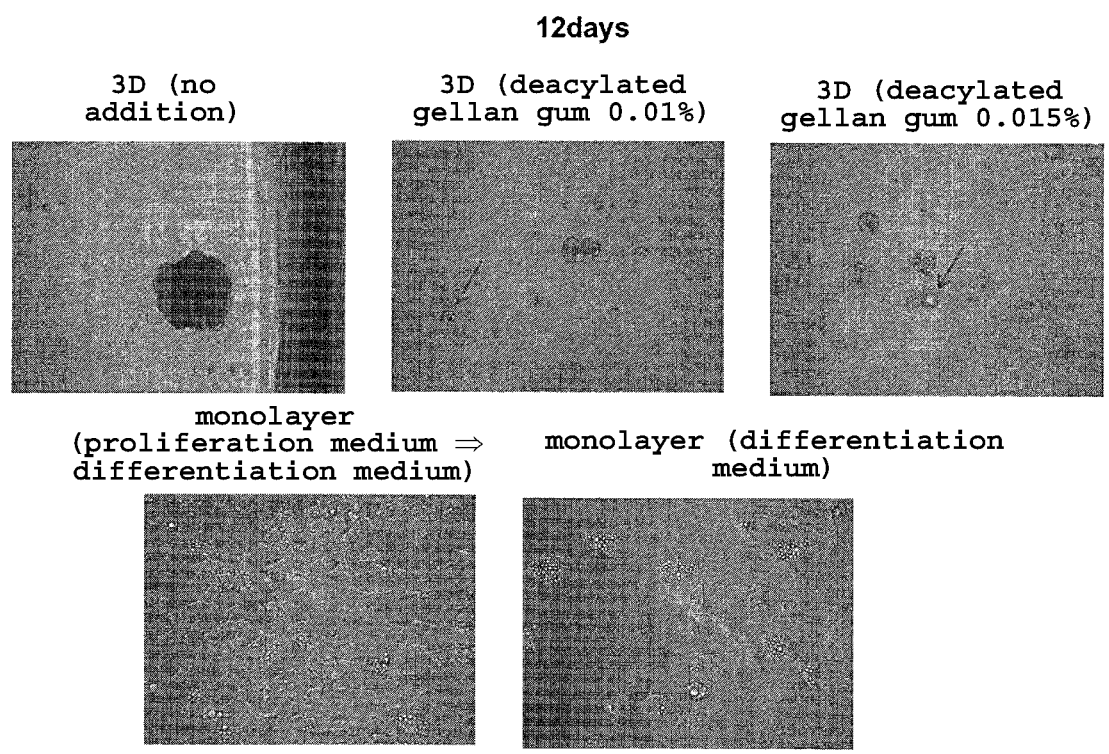
FIG. 1 shows morphology of each cell on day 12 from the start of culture.

DESCRIPTION OF EMBODIMENTS (I) Medium Composition to be Used in the Present Invention The medium composition to be used in the present invention is a liquid medium composition permitting culturing cells or tissues by suspending them. The medium composition enables culturing desired cells (i.e., mesenchymal cells having differentiation potency into adipocytes) while maintaining the suspended state. The medium composition can be prepared according to the descriptions of WO 2014/017513 A1 and US 2014/0106348 A1. In the following, the medium composition is sometimes referred to as medium composition I.

Suspending of cells or tissues in the present invention refers to a state where cells or tissues do not adhere to a culture vessel (non-adhesive). In the present invention, when the cells or tissues are cultured, the state where the cells or tissues are uniformly dispersed and suspended in the liquid medium composition in the absence of a pressure on or vibration of the liquid medium composition from the outside or shaking, rotating operation and the like in the medium composition is referred to as "static suspension", and cultivation of the cells or tissues in such condition is referred to as "static suspension culture". In the "static suspension", the period of suspending includes not less than 5 min, not less than 1 hr, not less than 24 hr, not less than 48 hr, not less than 7 days etc., though the period is not limited thereto as long as the suspended state is maintained.

The medium composition I permit static suspension of cells or tissues at least on one point in the temperature range (e.g., 0 to 40° C.) capable of culturing cells or tissues. The medium composition to be used in the present invention permits static suspension of cells or tissues at least at one point in the temperature range of preferably 25 to 37° C., most preferably 37° C.

Whether or not static suspension is possible can be evaluated by, for example, uniformly dispersing the cells to be cultured (i.e., mesenchymal cells having differentiation potency into adipocytes) in a medium composition to be evaluated at a concentration of $2 \times 10^4$ cells/ml, injecting 10 ml thereof in a 15 ml conical tube, standing the tube for at least not less than 5 min (e.g., not less than 1 hr, not less than 24 hr, not less than 48 hr, not less than 7 days) at 37° C., and observing whether the suspended state of the cells is maintained. When not less than 70% of the total cells are in a suspended state, it is defined in the present specification that the suspended state was maintained. Polystyrene beads (Size 500-600 μm, manufactured by Polysciences Inc.) may be used for evaluation instead of the cells The medium composition I contains a polymer compound having an anionic functional group or a salt thereof that can form a structure capable of suspending cells or tissues by binding via a divalent metal cation. In the medium composition used in the present invention, the polymer compound binds via a divalent metal cation to form three-dimensional networks (structure with indefinite shape) dispersed in water. When cells are cultured in a liquid medium containing the three-dimensional networks, the three-dimensional networks function as a carrier in suspending the cells, and the cells in the medium are trapped by the three-dimensional networks and do not sink. Thus, it is possible to culture the cells while uniformly dispersing the cells in a floating state (static suspension culture) without requiring shaking, a rotating operation or the like.

In one embodiment, the viscosity of the medium composition I is not more than 8 mPa·s, preferably not more than 4 mPa·s, more preferably not more than 2 mPa·s, at 37° C. The viscosity of the medium composition can be measured, for example, under 37° C. conditions and using an E-type viscosity meter (manufactured by Toki Sangyo Co., Ltd., TV-22 type viscosity meter, model: TVE-22L, corn rotor: standard rotor 1°34'×R24, rotating speed 100 rpm). The medium composition I can perform suspension culture (preferably, static suspension culture) of cells and tissues at such a low viscosity, and is thus superior in the operability in passage and the like.

As the anionic functional group, a carboxy group, sulfo group, phosphate group and a salt thereof can be mentioned, with preference given to carboxy group or a salt thereof.

As a polymer compound to be used in the present invention, one having one or more kinds selected from the aforementioned anionic functional groups can be used.

Specific preferable examples of the polymer compound to be used in the present invention include, but are not limited to, polysaccharides wherein not less than 10 monosaccharides (e.g., triose, tetrose, pentose, hexose, heptose etc.) are polymerized, more preferably, acidic polysaccharides having an anionic functional group. The acidic polysaccharides here are not particularly limited as long as it has an anionic functional group in the structure thereof, and includes, for example, polysaccharides having a uronic acid (e.g., glucuronic acid, iduronic acid, galacturonic acid, mannuronic acid), polysaccharides having a sulfate group or phosphate group in a part of the structure thereof, and polysaccharides having the both structures, and includes not only naturally-obtained polysaccharides but also polysaccharides produced by microorganisms, polysaccharides produced by genetic engineering, and polysaccharides artificially synthesized using an enzyme. More specifically, examples thereof include polymer compounds composed of one or more kinds selected from the group consisting of hyaluronic acid, gellan gum, deacylated gellan gum (hereinafter sometimes to be referred to as DAG), rhamsan gum, diutan gum, xanthan gum, carageenan, hexuronic acid, fucoidan, pectin, pectic acid, pectinic acid, heparan sulfate, heparin, heparitin sulfate, keratosulfate, chondroitin sulfate, dermatan sulfate, rhamnan sulfate, alginic acid and a salt thereof. Polysaccharide preferably contains a glucuronic acid moiety (e.g., hyaluronic acid, DAG, diutan gum, xanthan gum or a salt thereof etc.). In another preferable embodiment, polysaccharide may be carrageenan, alginic acid or a salt thereof. More preferably, polysaccharide is DAG, diutan gum, xanthan gum or a salt thereof, and most preferably DAG in consideration of the ability to suspend cells or tissues at a low concentration.

The salt here includes, for example, salts with alkali metal such as lithium, sodium, potassium, salts with alkaline earth metals such as calcium, barium, magnesium, and salts with aluminum, zinc, copper, iron, ammonium, organic base and amino acid and the like.

The weight average molecular weight of these polymer compounds (polysaccharides etc.) is preferably 10,000 to 50,000,000, more preferably 100,000 to 20,000,000, still more preferably 1,000,000 to 10,000,000. For example, the molecular weight can be measured based on pullulan by gel permeation chromatography (GPC).

Furthermore, phosphorylated DAG can also be used. The phosphorylation can be performed by a known method.

In the present invention, plural kinds (preferably two kinds) of the above-mentioned polysaccharides can be used in combination. The kind of the combination of the polysaccharides is not particularly limited as long as the aforementioned structure is formed in a liquid medium, and the cells or tissues can be uniformly suspended (preferably suspended statically). Preferably, the combination includes at least DAG or a salt thereof. That is, a preferable combination of polysaccharides contains DAG or a salt thereof, and polysaccharides other than DAG and a salt thereof (e.g., xanthan gum, alginic acid, carageenan, diutan gum, methylcellulose, locust bean gum or a salt thereof). Examples of specific combination of polysaccharides include, but are not limited to, DAG and rhamsan gum, DAG and diutan gum, DAG and xanthan gum, DAG and carageenan, DAG and zanthan gum, DAG and locust bean gum, DAG and K-carageenan, DAG and sodium alginate, DAG and methylcellulose and the like.

The deacylated gellan gum is a linear polymer polysaccharide containing 4 molecules of sugars of 1-3 bonded glucose, 1-4 bonded glucuronic acid, 1-4 bonded glucose and 1-4 bonded rhamnose as the constituent unit, which is a polysaccharide of the following formula (I) wherein $R_1$, $R_2$ are each a hydrogen atom, and n is an integer of two or more. $R_1$ may contain a glyceryl group, $R_2$ may contain an acetyl group, and the content of the acetyl group and glyceryl group is preferably not more than 10%, more preferably not more than 1%.

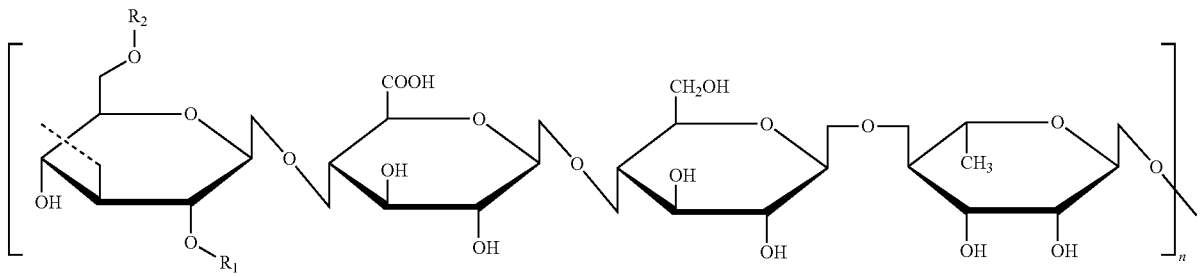

(I)

The concentration of the above-mentioned polymer compound in a medium depends on the kind of the polymer compound, and can be appropriately determined within the range where the polymer compound can form the aforementioned structure in a liquid medium, and can uniformly suspend (preferably statically suspend) the cells or tissues. It is generally 0.0005% to 1.0% (w/v), preferably 0.001% to 0.4% (w/v), more preferably 0.005% to 0.1% (w/v), still more preferably 0.005% to 0.05% (w/v). For example, in the case of deacylated gellan gum, it is added to a medium at 0.001% to 1.0% (w/v), preferably 0.003% to 0.5% (w/v), more preferably 0.0058% to 0.3% (w/v), more preferably 0.01% to 0.05% (w/v), most preferably, 0.01% to 0.03% (w/v). In the case of diutan gum and xanthan gum, it is added to a medium at 0.0018% to 5.0% (w/v), preferably 0.01% to 1.0% (w/v), more preferably 0.01% to 0.5% (w/v), most preferably 0.02% to 0.2% (w/v). In the case of a κ-carageenan and locust bean gum mixture, it is added to a medium at 0.001% to 5.0% (w/v), preferably 0.005% to 1.0% (w/v), more preferably 0.01% to 0.1% (w/v), most preferably 0.03% to 0.05% (w/v). In the case of native gellan gum, it is added to a medium at 0.05% to 1.0% (w/v), preferably 0.05% to 0.1% (w/v).

When plural kinds (preferably two kinds) of the above-mentioned polysaccharides are used in combination, the concentration of the polysaccharides can be appropriately set as long as they form the aforementioned structure in a liquid medium, and can uniformly suspend (preferably statically suspend) the cells or tissues. For example, when a combination of DAG or a salt thereof and polysaccharide other than DAG and a salt thereof is used, the concentration of DAG or a salt thereof is, for example, 0.005 to 0.02% (w/v), preferably 0.01 to 0.02% (w/v), and the concentration of a polysaccharide other than DAG and a salt thereof is, for example, 0.0001 to 0.4% (w/v), preferably 0.005 to 0.4% (w/v), more preferably 0.01 to 0.4% (w/v). Specific examples of the combination of the concentration range include the following.
DAG or a salt thereof: 0.005-0.02% (preferably 0.01-0.02%) (w/v)
polysaccharides other than DAG
xanthan gum: 0.01-0.4% (w/v)
sodium alginate: 0.0001-0.4% (w/v) (preferably, 0.1-0.4% (w/v))
native gellan gum: 0.0001-0.4% (w/v)
locust bean gum: 0.1-0.4% (w/v)
methylcellulose: 0.1-0.4% (w/v) (preferably 0.2-0.4% (w/v))
carrageenan: 0.05-0.1% (w/v)
diutan gum: 0.01-0.1% (w/v)

In one embodiment, DAG or a salt thereof is used in combination with alginic acid or a salt thereof (e.g., sodium alginate). The medium composition of this embodiment has property that it affords an effect of maintaining a suspended state of cells and tissues, as well as quickly losing the effect by adding chelating agent as necessary and applying a shear force by pipetting, filter filtration and the like (WO 2017/154952 A1).

The concentration of deacylated gellan gum or a salt thereof in the medium composition of this embodiment is, for example, 0.002 to 0.01 (w/v) %, preferably 0.002 to 0.009 (w/v) %, more preferably 0.003 to 0.009 (w/v) %. The concentration of alginic acid or a salt thereof in the medium composition of this embodiment is, for example, 0.004 to 0.1 (w/v) %, preferably 0.004 to 0.02 (w/v) %, more preferably 0.004 to 0.015 (w/v) %, further preferably 0.005 to 0.015 (w/v) %.

The mass ratio of the deacylated gellan gum or a salt thereof and the alginic acid or a salt thereof contained in the medium composition of this embodiment is not less than 1 part by mass, preferably not less than 2 parts by mass, of the alginic acid or a salt thereof per 1 part by mass of the deacylated gellan gum or a salt thereof. In one embodiment, the mass ratio is, for example, 1 to 4 parts by mass, preferably 1 to 3 parts by mass, more preferably 1 to 2 parts by mass, of the alginic acid or a salt thereof per 1 part by mass of the deacylated gellan gum or a salt thereof.

The concentration can be calculated by the following formula.

Concentration[% (w/v)]=weight(g) of particular compound/volume(ml) of medium composition×100

The medium composition I contains a divalent metal cation. Examples of the divalent metal cation include calcium ion, magnesium ion, zinc ion, manganese ion, ferric ion, copper ion and the like. The kind of the divalent metal cation is not particularly limited as long as the above-mentioned polymer compound can form a structure capable of suspending cells or tissues by binding via the divalent metal cation. It is preferred that the medium composition I contains at least one of a calcium ion and a magnesium ion, more preferably calcium ion. The concentration of the divalent metal cation in the medium composition I can be appropriately determined within the range where the above-mentioned polymer compound can form the aforementioned structure in a liquid medium, and can uniformly suspend (preferably statically suspend) the cells or tissues. For example, the concentration of calcium ion in the medium composition is, but is not limited to, 0.1 mM to 300 mM, preferably 0.5 mM to 100 mM. A typical liquid medium used for culturing mammals contains a calcium ion at a concentration sufficient for the above-mentioned polymer compound to form the aforementioned structure.

The medium composition I can be prepared by mixing a basal medium used for culturing cells and/or tissues with the aforementioned polymer compound. When the cells or tissues are derived from a mammal, any basal medium used for culturing mammalian cells can be used. Examples of such basal medium include Dulbecco's Modified Eagle's Medium (DMEM), HamF12 medium (Ham's Nutrient Mixture F12), DMEM/F12 medium, McCoy's 5A medium, Eagle MEM (Eagle's Minimum Essential Medium; EMEM), αMEM (alpha Modified Eagle's Minimum Essential Medium; αMEM), MEM (Minimum Essential Medium), RPMI1640 medium, Iscove's Modified Dulbecco's Medium (IMDM), MCDB131 medium, William medium E, IPL41 medium, Fischer's medium, StemPro34 (manufactured by Invitrogen), X-VIVO 10 (manufactured by Cambrex Corporation), X-VIVO 15 (manufactured by Cambrex Corporation), HPGM (manufactured by Cambrex Corporation), StemSpan H3000 (manufactured by STEMCELL Technologies), StemSpanSFEM (manufactured by STEMCELL Technologies), StemlineII (manufactured by Sigma Aldrich), QBSF-60 (manufactured by Qualitybiological), StemPro hESC SFM (manufactured by Invitrogen), Essential8 (registered trade mark) medium (manufactured by Gibco), mTeSR1 or 2 medium (manufactured by STEMCELL Technologies), ReproFF or ReproFF2 (manufactured by ReproCELL), PSGro hESC/iPSC medium (manufactured by System Biosciences), NutriStem (registered trade mark) medium (manufactured by Biological Industries), CSTI-7 medium (manufactured by Cell Science & Technology Institute, Inc.), MesenPRO RS medium (manufactured by Gibco), MF-Medium (registered trade mark) mesenchymal stem cell proliferation medium (manufactured by TOYOBO CO., LTD.), Sf-90011 (manufactured by Invitrogen), OptiPro (manufactured by Invitrogen), human adipocyte differentiation medium (manufactured by TOYOBO CO., LTD.), human adipocyte precursor proliferation medium (manufactured by TOYOBO CO., LTD.) and the like.

Those of ordinary skill in the art can freely add, according to the object, sodium, potassium, phosphorus, chlorine, various amino acids, various vitamins, antibiotic, serum (or alternative thereof), fatty acid, sugar and the like the above-mentioned medium. For culture of mammal-derived cells or tissues, those of ordinary skill in the art can also add, according to the object, one or more kinds of other chemical components and biogenic substances in combination.

Examples of the components to be added to a medium for mammal-derived cells (or tissues) include fetal bovine serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various hormones, various growth factors, various extracellular matrices, various cell adhesion molecules and the like.

The medium composition can be prepared according to the descriptions of WO 2014/017513A1, US2014/0106348 A1, WO 2017/154952 A1 and the like.

In a preferable embodiment, the medium composition I contains deacylated gellan gum or a salt thereof. In one embodiment, the concentration of deacylated gellan gum or a salt thereof in the medium composition is 0.001% to 1.0% (w/v), preferably 0.003% to 0.5% (w/v), more preferably 0.005% to 0.3% (w/v), further preferably 0.01% to 0.05% (w/v), most preferably 0.01% to 0.03% (w/v). The medium composition further contains a polysaccharide other than deacylated gellan gum or a salt thereof. The medium composition contains calcium ion at a as concentration sufficient for deacylated gellan gum to form the structure which enables culture of cells or tissues in suspension. The concentration is, for example, 0.1 mM to 300 mM, preferably, 0.5 mM to 100 mM. The viscosity of the medium composition my be not more than 8 mPa·s, preferably not more than 4 mPa·s, more preferably not more than 2 mPa·s, at 37° C.

In another preferable embodiment, the medium composition I contains deacylated gellan gum or a salt thereof, and alginic acid or a salt thereof (e.g., sodium alginate) in combination. In one embodiment, the concentration of the deacylated gellan gum or a salt thereof in the medium composition is, for example, 0.002 to 0.01 (w/v) %, preferably 0.002 to 0.009 (w/v) %, more preferably 0.003 to 0.009 (w/v) %. The concentration of the alginic acid or a salt thereof in the medium composition of this embodiment is, for example, 0.004 to 0.1 (w/v) %, preferably 0.004 to 0.02 (w/v) %, more preferably 0.004 to 0.015 (w/v) %, further preferably 0.005 to 0.015 (w/v) %. The mass ratio of the deacylated gellan gum or a salt thereof and the alginic acid or a salt thereof contained in the medium composition of this embodiment is not less than 1 part by mass, for example, 1 to 4 parts by mass, preferably 1 to 3 parts by mass, more preferably 1 to 2 parts by mass of alginic acid or a salt thereof, per 1 part by mass of the deacylated gellan gum or a salt thereof. The medium composition contains calcium ion at a concentration sufficient for deacylated gellan gum or alginic acid or a salt thereof to form the structure which enables culture of cells or tissues in suspension. The concentration is, for example, 0.1 mM to 300 mM, preferably, 0.5 mM to 100 mM. The viscosity of the medium composition my be not more than 8 mPa·s, preferably not more than 4 mPa·s, more preferably not more than 2 mPa·s, at 37° C.

(II) Production Method of Unilocular Adipocyte

The present invention provides a method for producing unilocular adipocytes comprising culturing mesenchymal cells having differentiation potency into adipocytes in suspension in the above-mentioned medium composition I to induce differentiation into unilocular adipocytes (hereinafter to be referred to as the production method 1 of the present invention).

The mesenchymal cell used for the present invention is a primary cell separated from the body of a mammal, a cell line established by passaging the primary cell, or a tumor cell. Examples of the mammal include rodents such as mouse, rat, hamster, guinea pig and the like, lagomorphs such as rabbit and the like, ungulates such as swine, bovine, goat, horse, sheep and the like, carnivora such as dog, cat and the like, primates such as human, monkey, *Macaca mulatta, Macaca fascicularis*, marmoset, orangutan, chimpanzee and the like, and the like. The mammal is preferably rodent (mouse etc.) or primate, more preferably human.

The mesenchymal cell means a cell constituting a connective tissue of bone, cartilage, fat, skeletal muscle, ligament, tendon and the like, or a stem cell or progenitor cell thereof, and is embryologically a mesoderm-derived cell. Examples of the mesenchymal cell having differentiation potency into adipocyte include, but are not limited to, adipocyte precursor, mesenchymal stem cell, fibroblast, dedifferentiated adipocyte and the like. The mesenchymal cell having differentiation potency into adipocyte to be used in the present invention is preferably an adipocyte precursor or a mesenchymal stem cell. In one embodiment, the mesenchymal cell having differentiation potency into adipocyte does not contain accumulation of fat droplets in the cell.

The precursor-adipocyte is an adipose tissue-derived cell having the ability to differentiate into adipocyte. Different ms from mature adipocytes, a precursor-adipocyte is free of intracellular accumulation of lipid droplets, and is a fibroblast-like cell having proliferation capacity. Generally, the expression level of at least a part of adipocyte marker genes in precursor-adipocyte is extremely low as compared with that in mature adipocytes. For example, the expression level of FABP4 mRNA in precursor-adipocyte can be not more than $1/10$, preferably not more than $1/100$, that of mature adipocytes. The expression level of PPAR gamma mRNA in precursor-adipocyte can be not more than $1/10$ that of mature adipocytes. The expression level of lipoprotein lipase (LPL) mRNA in precursor-adipocyte can be not more than $1/10$, preferably not more than $1/100$, that of mature adipocytes. Precursor-adipocyte can be isolated by digesting adipose tissues (subcutaneous adipose tissue, visceral fat tissue, etc.) excised from a mammal with a tissue-degrading enzyme such as collagenase to obtain a cell suspension, and fractionating the obtained cell suspension according to the method described in Int J Obes Relat Metab Disord. 1996 March; 20 Suppl 3:S77-83 and the like, for example, by centrifugation and the like, and collecting the precipitate as a fraction rich in precursor-adipocyte. Commercially available precursor-adipocyte may also be used. In addition, established precursor-adipocyte (e.g., 3T3-L1) may also be used.

The mesenchymal stem cell is a somatic stem cell having the ability to differentiate into adipocyte, osteoblast or chondrocyte, and further into platelet, liver or the like. The mesenchymal stem cell is a cell mainly derived from adipose tissue, bone marrow, or dental pulp. Different from mature adipocytes, mesenchymal stem cells do not show accumulation of lipid droplets in the cell and are fibroblast-like cells that show proliferation capacity. In general, in mesenchymal stem cells, the expression level of at least a part of adipocyte marker genes is extremely low as compared with mature adipocytes, as in the precursor-adipocyte described above. For example, adipose-derived mesenchymal stem cells can be isolated, like the precursor-adipocyte, by digesting adipose tissues (subcutaneous adipose tissue, visceral fat tissue, etc.) excised from a mammal with a tissue-degrading enzyme such as collagenase to obtain a cell suspension, and fractionating the obtained cell suspension according to the method described in Int J Obes Relat Metab Disord. 1996 March; 20 Suppl 3:S77-83 and the like, for example, by centrifugation and the like, and collecting the precipitate as a fraction rich in mesenchymal stem cells. Commercially available mesenchymal stem cells may also be used.

The unilocular adipocyte is an adipocyte containing only one large lipid droplet in one cell, and is also called white adipocyte. Different from precursor-adipocyte, mesenchymal stem cells, and organ-derived cells, these cells solely have property to float in a medium, saline and the like. This floating property is the same as that of adipocytes forming adipose tissue in the body. The unilocular adipocyte may be FABP4-positive, PPAR gamma-positive, and LPL-positive.

The medium composition I to be used for suspension culture to induce differentiation into unilocular adipocytes from mesenchymal cells having differentiation potency into adipocytes contains an adipocyte differentiation-inducing factor. As the adipocyte differentiation-inducing factor, a known one can be used. For example, at least one kind of factor selected from the group consisting of insulin, glucocorticoid receptor agonist, cAMP phosphodiesterase inhibitor, cyclooxygenase inhibitor, prostaglandin, long chain fatty acid, triiodothyronine, and PPARγ agonist, preferably two or more kinds of factors selected from the aforementioned group are used in combination. The glucocorticoid receptor agonist is not particularly limited and, for example, dexamethasone, cortisol, predonisolone, betamethasone, triamcinolone, triamcinolone acetonide, fluocinolone acetonide and the like can be mentioned, with preference given to dexamethasone. The cAMP phosphodiesterase inhibitor is not particularly limited and, for example, methylxanthines such as 3-isobutyl-1-methylxanthine and the like can be mentioned. The cyclooxygenase inhibitor is not particularly limited and, for example, indomethacin, aspirin and the like can be mentioned, with preference given to indomethacin. The prostaglandin is not particularly limited and, for example, $PGD_2$, $PGF_{2\alpha}$, $PGI_2$, $PGJ_2$ and the like can be mentioned, with preference given to $PGJ_2$. The long chain fatty acid is a generic term for fatty acids having a carbon number of eleven or more. Specifically, oleic acid, linoleic acid, palmitic acid, arachidonic acid and the like can be preferably used. The PPARγ agonist is not particularly limited, and thiazolidine derivatives such as pioglitazone, troglitazone, rosiglitazone and the like can be mentioned. Examples of a preferable combination of the adipocyte differentiation-inducing factors include, but are not limited to, insulin, glucocorticoid receptor agonist (dexamethasone etc.), and cyclooxygenase inhibitor (indomethacin etc.);

insulin, glucocorticoid receptor agonist (dexamethasone etc.), and cAMP phosphodiesterase inhibitor (3-isobutyl-1-methylxanthine etc.);

insulin, glucocorticoid receptor agonist (cortisol etc.), and triiodothyronine (T3) (DIABETES, 45, 1435-1438, 1996);

insulin, glucocorticoid receptor agonist (dexamethasone etc.), cyclooxygenase inhibitor (indomethacin etc.), and triiodothyronine (T3) and the like.

The concentration of the adipocyte differentiation-inducing factor to be added to the medium composition I is a concentration that induces differentiation of mesenchymal cells having differentiation potency into adipocytes into unilocular ms adipocytes (including white adipocytes or beige adipocytes), and a concentration generally used for inducing differentiation of adipocytes in the technical field can be applied to the present invention.

Insulin is added at a concentration of, for example, 1 to 100 μg/ml.

While different depending on the kind, the glucocorticoid receptor agonist (e.g., dexamethasone) is added at a concentration of, for example, 0.1 to 100 μM.

While different depending on the kind, the cAMP phosphodiesterase inhibitor (e.g., 3-isobutyl-1-methylxanthine) added at a concentration of, for example, 0.1 to 10 mM.

While different depending on the kind, the cyclooxygenase inhibitor (e.g., indomethacin) is added at a concentration of, for example, 0.01 to 1000 μM.

While different depending on the kind, prostaglandin (e.g., PGJ2) is added at a concentration of, for example, 1 to 100 μM While different depending on the kind, the long chain fatty acid (e.g., arachidonic acid) is added at a concentration of, for example, 0.5 to 500 μM.

While different depending on the kind, the PPARγ agonist (e.g., pioglitazone) is added at a concentration of, for example, 1 to 100 μM.

To promote differentiation into unilocular adipocytes (including white adipocytes or beige adipocytes) of mesenchymal cells having differentiation potency into adipocytes, the medium composition I optionally contains an epidermal growth factor (EGF). EGF is added at a concentration of, for example, 0.1 to 10 ng/ml.

To promote differentiation into unilocular adipocytes (including white adipocytes or beige adipocytes) of mesenchymal cells having differentiation potency into adipocytes, the medium composition I optionally contains transferrin. Transferrin includes serotransferrin and ovotransferrin. Transferrin is added at a concentration of, for example, 1 to 100 μg/ml.

To promote differentiation into unilocular adipocytes (including white adipocytes or beige adipocytes) of mesenchymal cells having differentiation potency into adipocytes, the medium composition I optionally contains triiodothyronine (T3). T3 is added at a concentration of, for example, 0.01 to 100 nM.

To promote differentiation of mesenchymal cells having differentiation potency into adipocytes into unilocular adipocytes (including white adipocyte and or beige adipocyte), the medium composition I optionally contains a serum (e.g., bovine calf serum, human serum) or an alternative thereof. The serum or an alternative thereof is added at a concentration of, for example, 0.1 to 20% (v/v).

In preferable one embodiment, the medium composition I contains insulin, a glucocorticoid receptor agonist (dexamethasone etc.), a cyclooxygenase inhibitor (indomethacin etc.), and EGF. In preferable one embodiment, the medium composition I contains insulin, a glucocorticoid receptor agonist (dexamethasone etc.), a cyclooxygenase inhibitor (indomethacin etc.), EGF, transferrin, and triiodothyronine.

In preferable one embodiment, the medium composition I contains insulin, a glucocorticoid receptor agonist (dexamethasone etc.), and a cAMP phosphodiesterase inhibitor (3-isobutyl-1-methylxanthine etc.).

In the production method 1 of the present invention, mesenchymal cells having differentiation potency into adipocytes are subjected to suspension culture (preferably stand suspension culture) in medium composition I containing the above-mentioned adipocyte differentiation-inducing factor.

For suspension culture of mesenchymal cells having differentiation potency into adipocytes, culture vessels generally used for cell culture such as flask, plastic bag, Teflon (registered trade mark) bag, dish, schale, dish for tissue culture, multidish, microplate, microwell plate, multiplate, multiwell plate, chamber slide, cell culture flask, spinner flask, tube, tray, culture bag, roller bottle and the like can be used for cultivation. These culture vessels are desirably low adhesive. As a non-cell-adhesive culture vessel, a culture vessel having a surface not artificially treated to improve adhesiveness to cells (e.g., coating treatment with extracellular matrix and the like), or a culture vessel having a surface artificially treated to reduce adhesiveness to cells can be used.

The suspension culture can also be performed by automatically conducting cell seeding, medium exchange, cell image acquisition, and recovery of cultured cells, under a mechanical control and under a closed environment while controlling pH, temperature, oxygen concentration and the like and using a bioreactor and an automatic incubator capable of high density culture.

Those of ordinary skill in the art can freely select the form and state of the mesenchymal cells to be cultured which have differentiation potency into adipocytes. Specific preferable examples thereof include, but are not particularly limited to, a state in which mesenchymal cells having differentiation potency into adipocytes are dispersed as single cells in medium composition I, a state in which mesenchymal cells having differentiation potency into adipocytes are attached to the surface of a carrier, a state in which mesenchymal cells having differentiation potency into adipocytes are embedded inside a carrier, a state in which plural mesenchymal cells having differentiation potency into adipocytes assemble and form cell aggregates (spheres (spheroid)) and the like. Mesenchymal cells having differentiation potency into adipocytes preferably in a state in which single cells are dispersed in medium composition I, or a state in which plural mesenchymal cells having differentiation potency into adipocytes assemble and form cell aggregates (spheres (spheroid)), are subjected to suspension culture (preferably, static suspension culture) in medium composition I. That is, preferably, a carrier for adhesion or embedding of mesenchymal cells having differentiation potency into adipocytes is not used.

When mesenchymal cells having differentiation potency into adipocytes are cultured by the production method 1 of the present invention, separately prepared mesenchymal cells having differentiation potency into adipocytes are added to the culture composition I containing the above-mentioned adipocyte differentiation-inducing factor, and suspended to achieve uniform dispersing. The suspending method is not particularly limited and, for example, manual suspending using pipetting and the like, suspending using instrument such as stirrer, vortex mixer, microplate mixer, shaking machine and the like can be mentioned. The obtained suspension of the mesenchymal cells having differentiation potency into adipocytes are seeded in a culture container, and subjected to suspension culture. The suspension culture may be performed statically, and may be accompanied by rotation, shaking, or stirring of the culture medium as necessary. The rotating speed and frequency can be appropriately set according to the object. Preferably, the cells are subjected to static suspension culture. When the medium composition needs to be exchanged during the culture, the cells and the medium are separated by centrifugation, filtration treatment or the like, and the cells are resuspended in medium composition I containing a fresh adipocyte differentiation-inducing factor and subjected to suspension culture. Alternatively, the cells are appropriately concentrated by centrifugation or filtration treatment, medium composition I containing a fresh adipocyte differentiation-inducing factor is added to the concentrate and the concentrate is subjected to suspension culture again.

In one embodiment, mesenchymal cells having differentiation potency into adipocytes are collected from maintenance culture (e.g., monolayer culture, suspension culture), and dispersed to single cells or a state close to single cells. Mesenchymal cells having differentiation potency into adipocytes are dispersed using an appropriate cell detachment solution. Examples of the cell detachment solution include EDTA; protease such as trypsin, collagenase IV, metalloprotease and the like, and the like, which can be used singly or in an appropriate combination. The dispersed mesenchymal cells having differentiation potency into adipocytes are suspended in the medium composition I containing an adipocyte differentiation-inducing factor, and subjected to suspension culture (preferably, static suspension culture). In the culture, the mesenchymal cells having differentiation potency into adipocytes may be in the state of single cells or sphere. It is preferable to use a non-cell-adhesive incubator for this culture, but the use is not limitative.

The concentration of the mesenchymal cells having differentiation potency into adipocytes at the time of start of the culture is not particularly limited as long as differentiation into unilocular adipocytes is induced by the method of the present invention. It is typically $1.0 \times 10^2$ to $1.0 \times 10^7$ cells/ml, preferably $1.0 \times 10^3$ to $1.0 \times 10^6$ cells/ml, more preferably $1.0 \times 10^4$ to $1.0 \times 10^5$ cells/ml (e.g., $3.0 \times 10^4$ to $9.0 \times 10^4$; cells/ml).

The temperature for culturing mesenchymal cells having differentiation potency into adipocytes is generally 25 to 39° C., preferably 37° C. The $CO_2$ concentration is generally, in culture atmosphere, 4 to 10% by volume, preferably 5% by volume. The oxygen concentration is, in culture atmosphere, 15 to 50% by volume, preferably 20% by volume.

Differentiation into unilocular adipocyte of mesenchymal cells having potency of adipocyte differentiation can be induced by suspension culture in the medium composition I containing an adipocyte differentiation-inducing factor. In a conventional method, an adipocyte differentiation-inducing factor is reacted with an precursor-adipocyte adhered on a plate, whereby only multilocular adipocytes with a spindle-like shape and containing intracellularly accumulated many small fat droplets, and adhered to the plate could be obtained. In contrast, by suspension culture of mesenchymal cells having differentiation potency into adipocytes in medium composition I containing an adipocyte differentiation-inducing factor according to the method of the present invention, spherical unilocular adipocytes suspended in the medium and containing large intracellular lipid droplet in one cell and more similar to a physiological state can be obtained. Induction of differentiation into unilocular adipocytes can be confirmed by observation of emergence of a cell having only one large lipid droplet in the cytoplasm under an optical microscope. In addition, the presence or absence of a lipid droplet in the cytoplasm can be performed using, for example, oil Red 0 staining method and the like. Alternatively, induction of differentiation into unilocular adipocytes may be confirmed by detection of the expression of adipocyte marker protein or an mRNA encoding same. The expression of an adipocyte marker protein can be performed by an immunological method (e.g., flow cytometry, immunohistochemistry etc.) using an antibody against the marker. The expression of an mRNA encoding an adipocyte marker can be performed by a well-known genetic engineering method such as RT-PCR and the like. Examples of the adipocyte marker include, but are not limited to, FABP4, PPAR gamma, LPL and the like. In one embodiment, the production method 1 of the present invention includes a step of confirming emergence of a unilocular adipocyte in the culture. In one embodiment, suspension culture of mesenchymal cells having differentiation potency into adipocytes in medium composition I containing an adipocyte differentiation-inducing factor is performed until a unilocular adipocyte emerges in the culture.

The culture period necessary for differentiation induction of mesenchymal cells having differentiation potency into adipocytes depends on the kind of the adipocyte inducer. It is generally not less than 8 days, preferably not less than 10 days, more preferably not less than 18 days, further preferably not less than 21 days, further more preferably not less than 30 days, from the start of suspension culture of the precursor-adipocyte cells.

In one embodiment, a unilocular adipocyte obtained by the production method 1 of the present invention is UCP-1 positive. UCP-1 is a beige adipocyte marker that controls energy consumption by promoting heat production. Therefore, the UCP-1 positive unilocular adipocyte may be an adipocyte having the phenotype of beige adipocyte (beige-like adipocyte). The beige adipocyte actively produced heat and consumes energy. Thus, transplantation of UCP-1 positive unilocular adipocytes obtained by the production method of this embodiment to patients with metabolic diseases such as diabetes, obesity and the like is expected to afford a prophylactic and/or therapeutic effect on the metabolic diseases. Induction of differentiation into UCP-1 positive unilocular adipocyte can be confirmed by detection of expression of UCP-1 protein or an mRNA encoding same. The expression of a UCP-1 protein can be performed by an immunological method (e.g., flow cytometry, immunohistochemistry etc.) using an antibody against UCP-1. The expression of UCP-1 mRNA can be performed by a well-known genetic engineering method such as RT-PCR and the like. In one embodiment, the production method 1 of the present invention includes a step of confirming emergence of a UCP-1 positive unilocular adipocyte in the culture. In one embodiment, suspension culture of mesenchymal cells having differentiation potency into adipocytes in medium composition I containing an adipocyte differentiation-inducing factor is continued until a UCP-1 positive unilocular adipocyte emerges in the culture, whereby UCP-1 positive unilocular adipocytes are obtained.

The culture period necessary for differentiation induction of UCP-1-positive unilocular adipocytes depends on the kind of the adipocyte inducer. It is generally, not less than 21 days, preferably not less than 30 days, more preferably not less than 36 days, from the start of suspension culture of the mesenchymal cells having differentiation potency into adipocytes.

Since unilocular adipocytes contain a large lipid droplet in the cytoplasm, they are spontaneously suspended in a liquid medium composition even when the medium composition does not contain a polymer compound having an anionic functional group that forms a structure capable of suspending cells or tissues by binding via the aforementioned divalent metal cation. Therefore, when the obtained unilocular adipocytes are continuously cultured in suspension after the emergence of unilocular adipocytes in a culture is confirmed and differentiation into more mature unilocular adipocytes are induced, the desired suspension culture can be continued even when the concentration of the polymer compound in the medium composition I is lowered. For example, at a stage when ms emergence of unilocular adipocytes is confirmed (e.g., at a stage of, for example, 8 to 30 days, preferably 18 to 30 days, from the start of suspension culture of mesenchymal cells having differentiation potency into adipocytes), the concentration of the polymer compound in a cell suspension obtained by suspension culture may be decreased to a concentration at which mesenchymal cells having differentiation potency into adipocytes cannot be suspended. For example, when deacylated gellan gum or a salt thereof alone is used as a polymer compound having an anionic functional group that forms a structure capable of suspending cells or tissues by binding via the aforementioned divalent metal cation, at a stage when emergence of unilocular adipocytes in a culture is confirmed (e.g., at a stage of, for example, 8 to 30 days, preferably 18 to 30 days, from the start of suspension culture of mesenchymal cells having differentiation potency into adipocytes), the concentration of deacylated gellan gum or a salt thereof in the medium composition is set to, for example, not more than 0.0075% (w/v), preferably not more than 0.00375% (w/v). When diutan gum or xanthan gum or a salt thereof is used as the polymer compound, the concentration thereof may be set to, for example, not more than 0.0158 (w/v), preferably not more than 0.0075% (w/v), at the stage when emergence of unilocular adipocytes in the culture is confirmed. The concentration of the polymer compound in the medium composition may be lowered stepwisely. For example, when deacylated gellan gum or a salt thereof is used as the polymer compound, for example, the concentration of deacylated gellan gum or a salt thereof in the medium composition is set to, for example, not more than 0.0075% (w/v) at a stage of, for example, 18 to 20 days from the start of suspension culture of mesenchymal cells having differentiation potency into adipocytes, and the concentration is further set to not more than 0.00375% (w/v) at a stage of 30 to 36 days from the start of suspension culture of mesenchymal cells having differentiation potency into adipocytes.

Induced unilocular adipocytes can be recovered by a well known method. Since unilocular adipocytes contain a large fat droplet in the cytoplasm, they are spontaneously suspended in a liquid medium composition even when the medium composition does not contain a polymer compound having an anionic functional group that forms a structure capable of suspending cells or tissues by binding via the aforementioned divalent metal cation. In addition, unilocular adipocytes do not form sediments even after centrifugation, and maintain a floating state in a liquid medium composition. Therefore, a cell suspension obtained by suspension culture is subjected to dilution and/or centrifugation in a liquid medium composition free of the above-mentioned polymer compound, and unilocular adipocytes maintaining the suspended state are recovered, whereby induced unilocular adipocytes can be isolated.

In one embodiment, the concentration of the polymer compound in a cell suspension obtained by suspension culture may be decreased to a concentration at which mesenchymal cells having differentiation potency into adipocytes cannot be suspended, and unilocular adipocytes maintaining the suspended state are recovered. For example, when deacylated gellan gum or a salt thereof alone is used as a polymer compound having an anionic functional group that forms a structure capable of suspending cells or tissues by binding via the aforementioned divalent metal cation, the concentration of deacylated gellan gum or a salt thereof in the medium composition is set to, for example, not more than 0.0075% (w/v), preferably not more than 0.003755% (w/v). After lowering the concentration of the polymer compound, the cell suspension may be subjected to centrifugation. By performing such operation, mesenchymal cells having differentiation potency into adipocytes which remain after suspension culture and the cells other than adipocytes free of a lipid droplet in the cell form sediments and the successfully differentiated unilocular adipocytes maintain a suspended state without forming sediments, the differentiated unilocular adipocytes can be easily separated from the remaining mesenchymal cells having differentiation potency into adipocytes and the cells other than adipocytes free of a fat droplet in the cell.

(III) Culture Preparation

The present invention provides a culture preparation containing
(1) mesenchymal cells having differentiation potency into adipocytes and/or unilocular adipocyte (including white adipocytes or beige adipocytes), and
(2) medium composition I.

In the culture preparation of the present invention, mesenchymal cells having differentiation potency into adipocytes and/or unilocular adipocytes (including white adipocytes or beige adipocytes) may be present in a suspended state in the medium composition I.

The mesenchymal cells having differentiation potency into adipocytes are preferably adipocyte precursors or mesenchymal stem cells.

The unilocular adipocyte may be UCP-1 positive.

In a preferable embodiment, the medium composition I contains deacylated gellan gum or a salt thereof. In one embodiment, the concentration of deacylated gellan gum or a salt thereof in the medium composition is 0.001% to 1.0% (w/v), preferably 0.003% to 0.5% (w/v), more preferably 0.005% to 0.3% (w/v), further preferably 0.01% to 0.05% (w/v), most preferably 0.018 to 0.03% (w/v). The medium composition may contain polysaccharides other than deacylated gellan gum or a salt thereof. The medium composition contains divalent calcium ion at a concentration sufficient for deacylated gellan gum to form the structure which enables culture of cells or tissues in suspension. The concentration is, for example, 0.1 mM to 300 mM, preferably, 0.5 mM to 100 mM. The viscosity of the medium composition may be not more than 8 mPa·s, preferably not more than 4 mPa·s, more preferably not more than 2 mPa·s, at 37° C.

In another preferable embodiment, medium composition I contains deacylated gellan gum or a salt thereof, and alginic acid or a salt thereof (e.g., sodium alginate) in combination. In one embodiment, the concentration of deacylated gellan gum or a salt thereof in the medium composition is, for example, 0.002 to 0.01 (w/v) %, preferably 0.002 to 0.009 (w/v) %, more preferably 0.003 to 0.009 (w/v) %. The concentration of alginic acid or a salt thereof in the medium composition of this embodiment is, for example, 0.004 to 0.1 (w/v) %, preferably 0.004 to 0.02 (w/v) %, more preferably 0.004 to 0.015 (w/v) %, further preferably 0.005 to 0.015 (w/v) %. The mass ratio of the deacylated gellan gum or a salt thereof and the alginic acid or a salt thereof contained in the medium composition of this embodiment is not less than 1 part by mass, for example, 1 to 4 parts by mass, preferably 1 to 3 parts by mass, more preferably 1 to 2 parts by mass of the alginic acid or a salt thereof, per 1 part by mass of the deacylated gellan gum or a salt thereof. The medium composition contains calcium ion at a concentration sufficient for deacylated gellan gum or a salt thereof and alginic acid or a salt thereof to form the structure which enables culture of cells or tissues in suspension. The concentration is, for example, 0.1 mM to 300 mM, preferably, 0.5 mM to 100 mM. The viscosity of the medium composition may be not more than 8 mPa·s, preferably not more than 4 mPa·s, more preferably not more than 2 mPa·s, at 37° C.

In a preferable embodiment, the medium composition I contains an adipocyte differentiation-inducing factor.

The adipocyte differentiation-inducing factor may be at least one kind of factor selected from the group consisting of insulin, glucocorticoid receptor agonist (e.g., dexamethasone), cAMP phosphodiesterase inhibitor (e.g., 3-isobutyl-1-methylxanthine), cyclooxygenase inhibitor (e.g., indomethacin), prostaglandin (e.g., $PGJ_2$), long chain fatty acid (e.g., arachidonic acid), triiodothyronine and PPARγ agonist (e.g., pioglitazone).

Preferably, the adipocyte differentiation-inducing factor contains any of the following combinations:
insulin, glucocorticoid receptor agonist (dexamethasone etc.), and cyclooxygenase inhibitor (indomethacin etc.);
insulin, glucocorticoid receptor agonist (dexamethasone etc.), and cAMP phosphodiesterase inhibitor (3-isobutyl-1-methylxanthine etc.);
insulin, glucocorticoid receptor agonist (cortisol etc.), and triiodothyronine; and
insulin, glucocorticoid receptor agonist (dexamethasone etc.), cyclooxygenase inhibitor (indomethacin etc.), and triiodothyronine.

The medium composition I may contain an epidermal growth factor (EGF) in addition to the adipocyte differentiation-inducing factor.

The medium composition I may contain transferrin.

The medium composition I may contain triiodothyronine.

The medium composition I may contain serum or an alternative thereof.

In one preferable embodiment, the medium composition I contains insulin, a glucocorticoid receptor agonist (dexamethasone etc.), a cyclooxygenase inhibitor (indomethacin etc.), and EGF. In one preferable embodiment, the medium composition I contains insulin, a glucocorticoid receptor agonist (dexamethasone etc.), a cyclooxygenase inhibitor (indomethacin etc.), EGF, transferrin, and triiodothyronine.

In one preferable embodiment, the medium composition I contains insulin, a glucocorticoid receptor agonist (dexamethasone etc.), and a cAMP phosphodiesterase inhibitor (3-isobutyl-1-methylxanthine etc.).

Unless particularly indicated, the definition of each term in (III) is the same as that described in the above-mentioned (I) and (II).

The contents disclosed in any publication cited herein, including patents and patent applications, are hereby incorporated in their entireties by reference, to the extent that they have been disclosed herein.

The present invention is explained in more detail in the following by concretely describing the Examples of the production method of the present invention and the evaluation method of the present invention; however, the present invention is not limited thereto.

EXAMPLE

Experimental Example 1: Differentiation Induction of Human Adipocyte Precursor into Adipocyte by 3D Culture Using Deacylated Gellan Gum Deacylated gellan gum (KELCOGEL CG-LA, manufactured by SANSHO Co., Ltd.) was suspended in ultrapure water (Milli-Q water) to 0.3 (w/v), and dissolved by stirring with heating at 90° C. The obtained aqueous solution was sterilized at 121° C. for 20 min in an autoclave. Using the solution, a medium composition was prepared by adding deacylated gellan gum at a final concentration of 0.010% or 0.015 (w/v) to a human adipocyte differentiation medium (#CAS11D250, manufactured by TOYOBO), or a no-addition medium composition free of deacylated gellan gum was prepared. As a 3D culture method using a low adhesion plate, a human precursor-adipocyte (derived from subcutaneous, #CAS02s05a, manufactured by TOYOBO) was seeded at 33333 cells/mL in the above-mentioned human adipocyte differentiation medium composition added or not added with deacylated gellan gum (no addition, 0.010%, 0.015%), and dispensed to the wells of a 96 well flat bottomed ultralow adhesion surface microplate (manufactured by Corning Incorporated, #3474) at 150 µL per well. The cells were cultured in a static state in a $CO_2$ incubator (37° C., 5% $CO_2$) for 12 consecutive days. As a monolayer culture method using a general plate to which human precursor-adipocyte can adhere, the cells were seeded at 5000 cells/mL in a human adipocyte differentiation medium or a human precursor-adipocyte proliferation medium (#CAS11K500, manufactured by TOYOBO), and dispensed to the wells of a 96 well flat bottomed ultralow adhesion surface microplate (manufactured by Corning Incorporated, #3585) at 150 µL per well. The cells seeded in the human adipocyte differentiation medium were cultured in a static state in a $CO_2$ incubator (37° C., 5% $CO_2$) for 12 consecutive days. On the other hand, the cells seeded in the human precursor-adipocyte proliferation medium were cultured in a static state in a $CO_2$ incubator (37° C., 5% $CO_2$) for 4 consecutive days, the medium was exchanged with a human adipocyte differentiation medium and further cultured for 12 consecutive days. After completion of the culture, photographs were taken.

As a result, when differentiation was induced by monolayer culture, multilocular adipocytes composed of small lipid droplets, having a spindle-like morphology, and adhered to the bottom surface of the plate were observed. On the other hand, under the condition of culturing under 3D conditions, large aggregates were observed due to aggregation of the cells under the condition of no addition of deacylated gellan gum. On the other hand, aggregation of the cells was suppressed under the 3D condition with the addition of deacylated gellan gum, and the presence of unilocular adipocyte-like cells containing lipid droplets was confirmed. The cell morphology under each culture condition is shown in FIG. 1.

Experimental Example 2: Differentiation Induction into Adipocyte by 3D Culture Using Deacylated Gellan Gum Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. The obtained aqueous solution was sterilized at 121° C. for 20 min in an autoclave. Using the solution, a medium composition was prepared by adding deacylated gellan gum at a final concentration of 0.015% (w/v) to a human adipocyte differentiation medium (#CAS11D250, manufactured by TOYOBO). As 3D culture using a low adhesion plate, a human precursor-adipocyte (derived from under a skin, #CAS02s05a, manufactured by TOYOBO) was seeded at 30000 cells/mL in the above-mentioned human adipocyte differentiation medium composition added with deacylated gellan gum (0.015%), and dispensed to the wells of a 6 well flat bottomed ultralow adhesion surface microplate (manufactured by Corning Incorporated, #3471) at 5 mL per well. The cells were cultured for 8 consecutive days. Except for wells used for mRNA analysis, the cell suspensions in the remaining wells were each placed in a 15 mL tube, subjected to a centrifugation operation (400 g, 3 min), and divided into a supernatant part (2.5 mL) and a sediment part (2.5 mL), human adipocyte differentiation medium composition (2.5 mL) free of deacylated gellan gum was added to each cell suspension, and the mixture was reseeded in each well. The cells were cultured in a static state in a $CO_2$ incubator (37° C., 5% $CO_2$) up to day 18 from the start of culture, i.e., for 10 days after reseeding. The name of the sample of the supernatant part cultured continuously was sup (10⇒018), and the name of the sample of the sediment part cultured continuously was bottom (10⇒18). On day 18 from the start of culture. The wells used for mRNA analysis were removed, the cell suspensions in the remaining wells were each placed in a 15 mL tube, subjected to a centrifugation operation (400 g, 3 min), and divided into a supernatant part (2.5 mL) and a sediment part (2.5 mL), human adipocyte differentiation medium composition (2.5 mL) free of deacylated gellan gum was added to each cell suspension, and the mixture was re-re-seeded in each well, and cultured up to day 26 from the start of culture, i.e., for 8 days after re-re-seeding. The fat-like cells, sup (10⇒18), already present in the supernatant part were continuously cultured in a suspended state and the sample name was designated as sup (10⇒26); the bottom (10⇒18) sample was cultured, the supernatant part was separated by centrifugation and continuously cultured and the sample name was designated as sup (18⇒26), and the sediment part was separated and continuously cultured, and the sample was designated as bottom (10⇒26).

In the mRNA analysis, in the sediment part and bottom (10⇒18) and bottom (10⇒26) samples, the cultures were recovered and centrifuged (400 g, 3 min) to collect the cells. Using RNeasy Mini kit (manufactured by QIAGEN), the total RNA was extracted from the cells. In the supernatant part and sup (10⇒18), sup (10⇒26), sup (18⇒26) samples, the cells suspended in the culture medium were collected with a pipette while containing the medium and the total RNA was extracted using RNeasy Mini kit (manufactured by QIAGEN). Using total RNA and PrimeScript™RT Master Mix (manufactured by Takara Bio Inc.) and GeneAmp PCR System 9700 (manufactured by Applied Biosystems), a reverse transcription reaction was performed to synthesize cDNA. Each cDNA sample was dispensed, diluted ⅒ with sterile water and used for PCR. As a sample to be used for analytical curve, dispensed and mixed cDNA was used, and a quantification range was set at common ratio 3 and from ⅓ to ½₄₃ dilution. PCR was performed using each cDNA sample, calibration sample, Premix Ex Taq™ (manufactured by Takara Bio Inc.), various TaqMan probes (manufactured by Applied Biosystems), and 7500 Real Time PCR System (manufactured by Applied Biosystems). Using mRNA of PPIA (cyclophilin B) as an endogenous control, the expression of PPAR gamma mRNA or FABP4 mRNA was normalized with the PPIA value. Each probe (manufactured by Applied Biosystems) used is shown below.

PPIA: HS99999904
PPAR gamma: HS011155134
FABP4: HS01086177

As a result, when human precursor-adipocyte was induced to differentiate into adipocyte using the medium composition of the present invention, the mRNA expression levels of PPAR gamma and FABP4, which were adipocyte markers in the cells, increased. In addition, the cells floating in the supernatant after the centrifugation operation could be collected by lowering the polysaccharide concentration. It was suggested that the suspended cell population shows particularly high expression level of PPAR gamma mRNA and contains highly differentiated adipocytes. The mRNA expression values of PPAR gamma and FABP4 are shown in Table 1.

TABLE 1

| days of culture | deacylated gellan gum concentration (%) | sample name | FABP4 (PPIA normalized value) | PPAR gamma (PPIA normalized value) |
|---|---|---|---|---|
| day 0  | 0.015   | day 0           | 0.001 | 0.36  |
| day 8  | 0.015   | day 8           | 4.39  | 4.54  |
| day 18 | 0.0075  | sup (10⇒18)     | 5.28  | 5.58  |
| day 18 | 0.0075  | bottom(10⇒18)   | 4.61  | 4.79  |
| day 26 | 0.00375 | sup(10⇒26)      | 6.10  | 20.26 |
| day 26 | 0.00375 | sup(10⇒18)      | 5.17  | 8.11  |
| day 26 | 0.00375 | bottom(10⇒26)   | 4.51  | 4.88  |

Experimental Example 3: Differentiation Induction into Adipocyte by 3D Culture Using Deacylated Gellan Gum Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. The obtained aqueous solution was sterilized at 121° C. for 20 min in an autoclave. Using the solution, a medium composition was prepared by adding deacylated gellan gum at a final concentration of 0.015% (w/v) to a human adipocyte differentiation medium (#CAS11D250, manufactured by TOYOBO). As 3D culture using a low adhesion plate, a human precursor-adipocyte (derived from under a skin, #CAS02s05a, manufactured by TOYOBO) was seeded at 30000 cells/mL in the above-mentioned human adipocyte differentiation medium composition added with deacylated gellan gum (0.015%), and dispensed to the wells of a 6 well flat bottomed ultralow adhesion surface microplate (manufactured by Corning Incorporated, #3471) at 5 mL per well. The cells were cultured in a static state in a $CO_2$ incubator (37° C., 5% $CO_2$) for 10 consecutive days. Except for wells used for mRNA analysis, the cell suspensions in the remaining wells were each placed in a 15 mL tube, subjected to a centrifugation operation (400 g, 3 min), a sediment part (2.5 mL) alone was separated, human adipocyte differentiation medium composition (2.5 mL) free of deacylated gellan gum was added to each cell suspension, and the mixture was reseeded in each well. The cells were cultured in a static state in a $CO_2$ incubator (37° C., 5% $CO_2$) and continuously cultured up to day 20 from the start of culture, i.e., for 10 days after reseeding. On day 20 from the start of culture, the cell suspension was placed in a 15 mL tube, subjected to a centrifugation operation (400 g, 3 min), divided into a supernatant part (2.5 mL) and a sediment part (2.5 mL), and respectively used for mRNA analysis (sample name: sup20 and bottom20). The cell suspension in another well was subjected to a centrifugation operation (400 g, 3 min), the supernatant part (2.5 mL) was separated, the human adipocyte differentiation medium composition (2.5 mL) free of deacylated gellan gum was added to each cell suspension, and the mixture was re-re-seeded in each well. The cells were cultured in a static state in a $CO_2$ incubator (37° C., 59 $CO_2$) up to day 30 from the start of culture, i.e., for 10 days after re-re-seeding. Sup20 already present in the supernatant part was continuously cultured and the sample name was designated as sup (20⇒30).

In the mRNA analysis, in the sediment part and bottom 20 samples, the cultures were centrifuged (400 g, 3 min) to collect the cells. Using RNeasy Mini kit (manufactured by QIAGEN), the total RNA was extracted from the cells. In the supernatant part and sup 20 and sup (20⇒30) samples, the cells suspended in the culture medium were collected with a pipette while containing the medium and the total RNA was extracted using RNeasy Mini kit (manufactured by QIAGEN). Using total RNA and PrimeScript™RT Master Mix (manufactured by Takara Bio Inc.) and GeneAmp PCR System 9700 (manufactured by Applied Biosystems), a reverse transcription reaction was performed to synthesize cDNA. Each cDNA sample was dispensed, diluted ⅒ with sterile water and used for PCR. As a sample to be used for analytical curve, dispensed and mixed cDNA was used, and a quantification range was set at common ratio 3 and from ⅓ to ½₄₃ dilution. PCR was performed using each cDNA sample, calibration sample, Premix Ex Taq™ (manufactured by Takara Bio Inc.), various TaqMan probes (manufactured by Applied Biosystems), and 7500 Real Time PCR System (manufactured by Applied Biosystems). Using mRNA of PPIA (cyclophilin B) as an endogenous control, the expression of PPAR gamma mRNA or lipoprotein lipase (LPL)

mRNA was normalized with the PPIA value. Each probe (manufactured by Applied Biosystems) used is to shown below.
PPIA: HS99999904
PPAR gamma: HS011155134
LPL: HS00173425

[Intracellular Fat Droplet Staining by Oil-Red Method]

Using the sup (20⇒30) cells described above, intracellular fat droplets were stained by the oil-Red method. The cell suspension (3 μL) was added dropwise onto a slide glass with a detachment prevention treatment (APS coat manufactured by Matsunami Glass), and 2 μL of a reagent 1 solution (Smear Gell, #SG-01, manufactured by Funakoshi) was added and pipetting was performed. Then, 5 μL of a reagent 2 solution (Smear Gell, #SG-01, manufactured by Funakoshi) was added, and the mixture was rapidly pipetted twice, spread on the slide glass as it was, and left standing for about 2 min to allow for solidification. Then, 75 μL of Diluted Lipid Droplets Assay Fixative (adipogenesis assay kit, #10006908, manufactured by Cayman Chemical Company) was added dropwise, and the mixture was allowed to stand for 15 min. Furthermore, 100 μL of Wash Solution (adipogenesis assay kit, #10006908, manufactured by Cayman Chemical Company) was added dropwise and the mixture was left standing for 5 min. After repeating this operation twice, the Wash Solution was removed and the sample was dried at room temperature. Then, 5 μL of Oil Red O (adipogenesis assay kit, #10006908, manufactured by Cayman Chemical Company) was added dropwise, and the mixture was left standing for about 20 min and then washed with distilled water. This washing operation was repeated until the washing liquid did not turn pink. The Wash Solution (adipogenesis assay kit, #10006908, manufactured by Cayman Chemical Company, 100 μL) was added dropwise, and the mixture was left standing for about 5 min. After repeating this operation twice, the Wash Solution was removed and the sample was dried at room temperature. Then, microscopic observation was performed.

Figure 2:
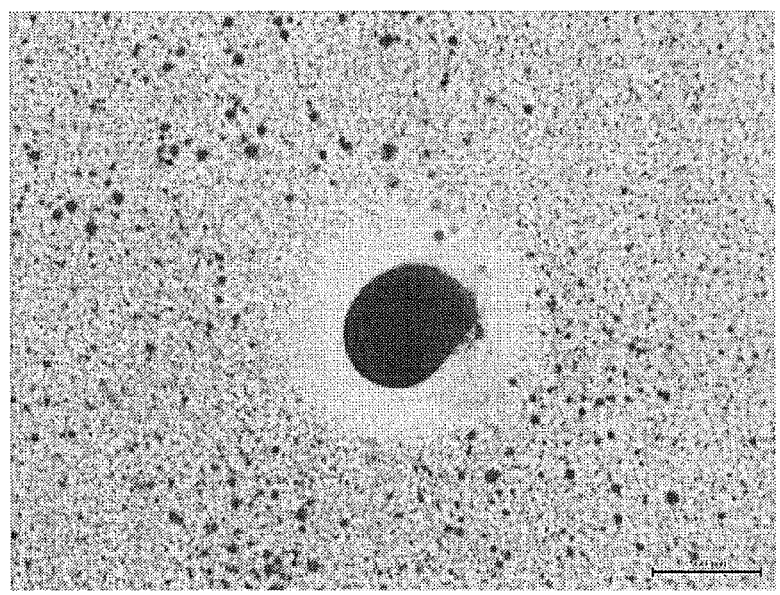
FIG. 2 shows an oil Red staining image of a differentiated adipocyte on day 30 from the start of culture.

As a result, when human precursor-adipocyte was induced to differentiate into adipocyte using the medium composition of the present invention, the mRNA expression levels of PPAR gamma and LPL, which were adipocyte markers in the cells, increased. The adipocyte differentiated by this method contains unilocular lipid droplet by oil Red staining, and shows high expression levels of PPAR gamma mRNA and LPL mRNA. Thus, it was suggested that the adipocyte is a highly differentiated adipocyte. The mRNA expression values of PPAR gamma and LPL are shown in Table 2, and an adipocyte image by oil Red staining is shown in FIG. 2.

TABLE 2

| days of culture | deacylated gellan gum concentration (%) | sample name | LPL (PPIA normalized value) | PPAR gamma (PPIA normalized value) |
|---|---|---|---|---|
| day 0 | 0.015 | day 0 | 0 | 0.32 |
| day 10 | 0.015 | day 8 | 3.29 | 2.78 |
| day 20 | 0.0075 | sup 20 | 7.43 | 11.05 |
| day 20 | 0.0075 | Bottom20 | 12.63 | 5.06 |
| day 30 | 0.00375 | sup(20⇒30) | 15.33 | 7.84 |

Experimental Example 4: Differentiation Induction into Adipocyte by 3D Culture Using Deacylated Gellan Gum and UCP-1 Expression Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. The obtained aqueous solution was sterilized at 121° C. for 20 min in an autoclave. Using the solution, a medium composition was prepared by adding deacylated gellan gum at a final concentration of 0.015% (w/v) to a human adipocyte differentiation medium (#CAS11D250, manufactured by TOYOBO). Successively, as 3D culture method using a low adhesion plate, a human precursor-adipocyte (derived from subcutaneous, #CAS02s05a, manufactured by TOYOBO) was seeded at 90000 cells/mL in the above-mentioned human adipocyte differentiation medium composition added with deacylated gellan gum (0.015%), and dispensed to the wells of a 6 well flat bottomed ultralow adhesion surface microplate (manufactured by Corning Incorporated, #3471) at 5 mL per well. The cells were cultured in a static state in a $CO_2$ incubator (37° C., 57 $CO_2$) for 10 consecutive days. The cell suspensions in respective wells were each placed in a 50 mL tube, the evaporated amount of the medium was supplemented with sterile water, human adipocyte differentiation medium composition (5 mL) free of deacylated gellan gum was added, and the mixture was reseeded in the wells. The cells were continuously cultured in a static state in a $CO_2$ incubator (37° C., 5% $CO_2$) up to day 21 from the start of culture, i.e., for 11 days after reseeding. On day 21 from the start of culture, the cell suspension was placed in a 15 mL tube, subjected to a centrifugation operation (400 g, 3 min), divided into a supernatant part (5 mL) and a sediment part (5 mL), and respectively used for mRNA analysis (sample name: sup21 and bottom21). The cell suspension in another well was placed in a 50 mL tube, the evaporated amount of the medium was supplemented with sterile water, the human adipocyte differentiation medium composition (10 mL) free of deacylated gellan gum was added, and the mixture was re-re-seeded in each well. The cells were cultured in a static state in a $CO_2$ incubator (37° C., 5% $CO_2$) up to day 36 from the start of culture, i.e., for 15 days after re-re-seeding. On day 36 from the start of culture, the cell suspension was placed in a 50 mL tube, subjected to a centrifugation operation (400 g, 3 min), divided into a supernatant part (10 mL) and a sediment part (10 mL), and respectively used for mPRNA analysis (sample name: sup36 and bottom36).

In the mRNA analysis, in the sediment part and bottom 20 samples, the cultures were centrifuged (400 g, 3 min) to collect the cells. Using RNeasy Mini kit (manufactured by QIAGEN), the total RNA was extracted from the cells. In the supernatant part and sup 20 and sup (20⇒30) samples, the cells suspended in the culture medium were collected with a pipette while containing the medium and the total PRNA was extracted using RNeasy Mini kit (manufactured by QIAGEN). Using total RNA and PrimeScript™RT Master Mix (manufactured by Takara Bio Inc.) and GeneAmp PCR System 9700 (manufactured by Applied Biosystems), a reverse transcription reaction was performed to synthesize cDNA. Each cDNA sample was dispensed, diluted ¹⁄₁₀ with sterile water and used for PCR. As a sample to be used for analytical curve, dispensed and mixed cDNA was used, and a quantification range was set at common ratio 3 and from ⅓ to ¹⁄₂₄₃ dilution. PCR was performed using each cDNA sample, calibration sample, Premix Ex Taq™ (manufactured by Takara Bio Inc.), various TaqMan probes (manufactured by Applied Biosystems), and 7500 Real Time PCR System (manufactured by Applied Biosystems). Using mRNA of PPIA (cyclophilin B) as an endogenous control, the expression of PPAR gamma mRNA or UCP-1 mRNA was normalized with the PPIA value. Each probe (manufactured by Applied Biosystems) used is shown below.

PPIA: HS99999904
PPAR gamma: HS011155134
TJCP-1: HS00222453

[Intracellular Fat Droplet Staining by Oil-Red Method]

Using the bottom36 cells described above, intracellular fat droplets were stained by the oil-Red method. The cell suspension (3 μL) was added dropwise onto a slide glass with a peeling prevention treatment (APS coat manufactured by Matsunami Glass), and 2 μL of a reagent 1 solution (Smear Gell, #SG-01, manufactured by Funakoshi) was added and pipetting was performed. Then, 5 μL of a reagent 2 solution (Smear Gell, #SG-01, manufactured by Funakoshi) was added, and the mixture was rapidly pipetted twice, spread on the slide glass as it was, and left standing for about 2 min to allow for solidification. Then, 75 μL of Diluted Lipid Droplets Assay Fixative (adipogenesis assay kit, #10006908, manufactured by Cayman Chemical Company) was added dropwise, and the mixture was allowed to stand for 15 min. Furthermore, 100 μL of Wash Solution (adipogenesis assay kit, #10006908, manufactured by Cayman Chemical Company) was added dropwise and the mixture was left standing for 5 min. After repeating this operation twice, the Wash Solution was removed and the sample was dried at room temperature. Then, 5 μL of Oil Red 0 (adipogenesis assay kit, #10006908, manufactured by Cayman Chemical Company) was added dropwise, and the mixture was left standing for about 20 min and then washed with distilled water. This washing operation was repeated until the washing liquid did not turn pink. The Wash Solution (adipogenesis assay kit, #10006908, manufactured by Cayman Chemical Company, 100 μL) was added dropwise, and the mixture was left standing for about 5 min. After repeating this operation twice, the Wash Solution was removed and the sample was dried at room temperature. Then, microscopic observation was performed.

Figure 3:
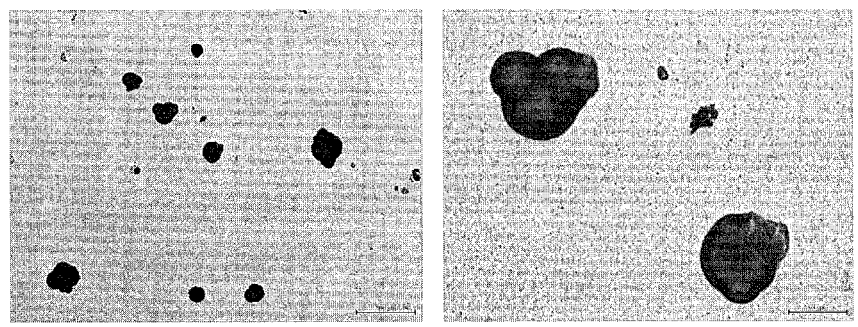
FIG. 3 shows oil Red staining images of differentiated adipocytes on day 36 from the start of culture.

As a result, when human precursor-adipocyte was induced to differentiate into adipocyte using the medium composition of the present invention under the conditions of seeding at a cell density 3 times that in Example 2, the mPRNA expression level of PPAR gamma, which is an adipocyte marker in the cells, increased. The adipocyte differentiated by this method contains unilocular lipid droplet by oil Red staining, and several differentiated adipocytes were coagulated. In addition, the expression of UCP-1 mRNA which is a beige adipocyte marker that controls heat production increased, and showed the maximum value on day 36. When differentiation into adipocyte was induced by the present method, a beige-like adipocyte which is unilocular, shows high expression level of PPAR gamma mRNA, and further shows an increased expression of UCP-1 that controls heat production was suggested. The mRNA expression values of PPAR gamma and UCP-1 are shown in Table 3, and an adipocyte image by oil Red staining is shown in FIG. 3.

TABLE 3

| days of culture | deacylated gellan gum concentration (%) | sample name | UPC-1 (PPIA normalized value) | PPAR gamma (PPIA normalized value) |
|---|---|---|---|---|
| day 0 | 0.015 | day 0 | 0 | 0.056 |
| day 21 | 0.0075 | Sup 21 | 1.167 | 1.569 |
| day 21 | 0.0075 | Bottom 21 | 0.856 | 1.492 |
| day 36 | 0.00375 | Sup36 | 4.112 | 1.632 |
| day 36 | 0.00375 | Bottom 36 | 4.970 | 1.706 |

Experimental Example 5: Differentiation Induction into Adipocyte by 3D Culture Using Deacylated Gellan Gum and Each so Differentiation Induction Medium in Combination, and UCP-1 Expression Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. The obtained aqueous solution was sterilized at 121° C. for 20 min in an autoclave. Using the solution, a medium composition was prepared by adding deacylated gellan gum at a final concentration of 0.015% (w/v) to a human adipocyte differentiation medium (#CAS11D250, manufactured by TOYOBO) or DMEM medium (manufactured by WAKO) containing 10% (v/v) fetal bovine serum (FBS), 1 μg/mL insulin, 2 μM dexamethasone, and 500 μM 3-isobutyl-1-methylxanthine (IDI differentiation induction material, Takara, Takara-Bio AdipoInducer Reagent). Successively, as 3D culture method using a low adhesion plate, a human precursor-adipocyte (derived from subcutaneous, #CAS02s05a, manufactured by TOYOBO) was suspended at 90000 cells/mL in the above-mentioned human adipocyte differentiation medium composition added with deacylated gellan gum (0.015%) or 10% FBS-containing IDI differentiation medium composition (0.015%), and dispensed to the wells of a 6 well flat bottomed ultralow adhesion surface microplate (manufactured by Corning Incorporated, #3471) at 5 mL per well. The cells were cultured in a static state in a $CO_2$ incubator (37° C., 5% $CO_2$) for 10 consecutive days. The cell suspensions in respective wells were each placed in a 50 mL tube, the evaporated amount of the medium was supplemented with sterile water, human adipocyte differentiation medium composition (5 mL) free of deacylated gellan gum or 10% FBS-containing IDI differentiation medium composition (5 mL) was added, and the mixture was reseeded in the wells. The cells were continuously cultured in a static state in a $CO_2$ incubator (37° C., 5% $CO_2$) up to day 20 from the start of culture, i.e., for 10 days after reseeding. On day 20 from the start of culture, the cell suspension in each well was placed in a 50 mL tube, the evaporated amount of the medium was supplemented with sterile water, a human adipocyte differentiation medium composition (10 mL) free of deacylated gellan gum or a 108 FBS-containing IDI differentiation medium composition (10 mL) was added, and the mixture was re-seeded in each well. The cells were cultured in a static state in a $CO_2$ incubator (37° C., 5% $CO_2$) up to day 31 and day 40 from the start of culture, i.e., for 11 days and 20 days after re-seeding. On day 10, day 20, day 31, and day 40 from the start of culture, the cell suspension was recovered from a part of respective wells and each was used for mRNA analysis.

In the mRNA analysis, the total RNA was extracted from the cell suspension also containing the medium using RNeasy Mini kit (manufactured by QIAGEN). Using total RNA and PrimeScript™RT Master Mix (manufactured by Takara Bio Inc.) and GeneAmp PCR System 9700 (manufactured by Applied Biosystems), a reverse transcription reaction was performed to synthesize cDNA. Each cDNA sample was dispensed, diluted 1/10 with sterile water and used for PCR. As a sample to be used for analytical curve, dispensed and mixed cDNA was used, and a quantification range was set at common ratio 3 and from 1/3 to 1/243 dilution. PCR was performed using each cDNA sample, calibration sample, Premix Ex Taq™ (manufactured by Takara Bio Inc.), various TaqMan probes (manufactured by Applied Biosystems), and 7500 Real Time PCR System (manufactured by Applied Biosystems). Using mRNA of PPIA (cyclophilin B) as an endogenous control, the expression of UCP-1 mRNA or PPAR gamma mRNA was normalized with the PPIA value. Each probe (manufactured by Applied Biosystems) used is shown below.

PPIA: HS99999904
PPAR gamma: HS011155134
UCP-1: HS00222453

Figure 4:
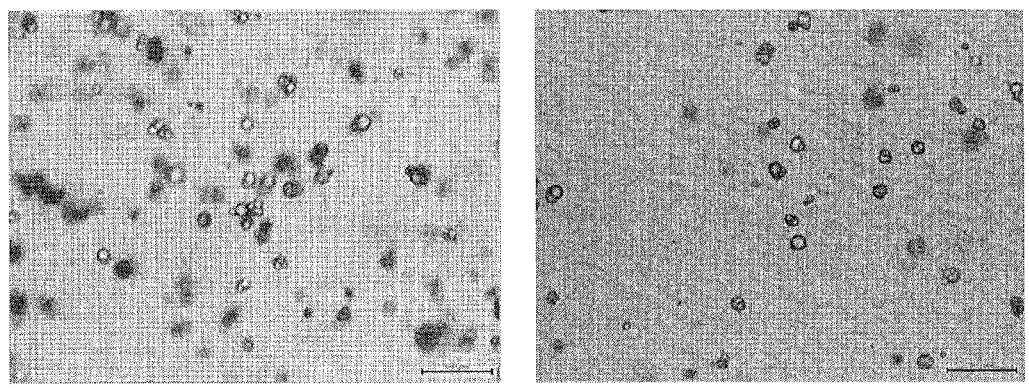
FIG. 4 shows morphology of cells on day 39 from the start of culture.

As a result, when a medium composition containing a general adipocyte differentiation-inducing factor IDI (insulin, dexamethasone, and 3-isobutyl-1-methylxanthine) in combination was used, emergence of unilocular adipocytes was found and the mRNA expression of adipocyte markers PPAR gamma and FABP4 increased. The expression of UCP-1 mRNA which is a beige adipocyte marker that controls heat production increased, and showed the maximum value on day 40. From these results, it was suggested that differentiation into unilocular beige-like adipocytes can be induced under various adipocyte differentiation induction conditions according to the production method of the present invention. The mRNA expression values of PPAR gamma and UCP-1 are shown in Table 4, and cell morphology on day 39 of differentiation induction is shown in FIG. 4.

TABLE 4

| days of culture | PPAR gamma (PPIA normalized value) | | UCP-1 (PPIA normalized value) | |
| --- | --- | --- | --- | --- |
| | TOYOBO differentiation medium | IDI differentiation medium | TOYOBO differentiation medium | IDI differentiation medium |
| day 0 | 0.63 | 0.50 | 0 | 0.01 |
| day 10 | 4.89 | 6.56 | 0.12 | 1.94 |
| day 20 | 4.29 | 6.29 | 0.90 | 9.34 |
| day 31 | 3.56 | 12.96 | 29.25 | 31.23 |
| day 40 | 15.20 | 6.07 | 20.22 | 124.49 |

Experimental Example 6: Differentiation Induction of Fat-Derived Mesenchymal Stem Cells into Adipocytes Using Deacylated Gellan Gum Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. The obtained aqueous solution was sterilized at 121° C. for 20 min in an autoclave. Using the solution, a medium composition was prepared by adding deacylated gellan gum at a final concentration of 0.015% (w/v) to a human adipocyte differentiation medium (#CAS11D250, manufactured by TOYOBO). Successively, as 3D culture method using a low adhesion plate, human fat-derived mesenchymal stem cells (C-12977, manufactured by Takara Bio Inc.) were suspended at 90000 cells/mL in the above-mentioned human adipocyte differentiation medium composition added with deacylated gellan gum (0.015%), and dispensed to the wells of a 6 well flat bottomed ultralow adhesion surface microplate (manufactured by Corning Incorporated, #3471) at 5 mL per well. The cells were cultured in a static state in a $CO_2$ incubator (37° C., 5% $CO_2$) for 10 consecutive days. The cell suspensions in respective wells were each placed in a 50 mL tube, the evaporated amount of the medium was supplemented with sterile water, human adipocyte differentiation medium composition (5 mL) free of deacylated gellan gum was added, and the mixture was reseeded in the wells. The cells were continuously cultured in a static state in a $CO_2$ incubator (37° C., 5% $CO_2$) up to day 20 from the start of culture, i.e., for 10 days after reseeding. On day 20 from the start of culture, the cell suspension in each well was placed in a 50 mL tube, the evaporated amount of the medium was supplemented with sterile water, human adipocyte differentiation medium composition (5 mL) free of deacylated gellan gum was added, and the mixture was reseeded in the wells. The cells were cultured in a static state in a $CO_2$ incubator (37° C., 5% $CO_2$) up to day 30 from the start of culture, i.e., for 10 days after re-seeding. On day 10, day 20, and day 30 from the start of culture, the cell suspension was recovered from a part of respective wells and each was used for mRNA analysis.

In the mRNA analysis, the total RNA was extracted from the cell suspension also containing the medium using RNeasy Mini kit (manufactured by QIAGEN). Using total RNA and PrimeScript™RT Master Mix (manufactured by Takara Bio Inc.) and GeneAmp PCR System 9700 (manufactured by Applied Biosystems), a reverse transcription reaction was performed to synthesize cDNA. Each cDNA sample was dispensed, diluted 1/10 with sterile water and used for PCR. As a sample to be used for analytical curve, dispensed and mixed cDNA was used, and a quantification range was set at common ratio 3 and from 1/3 to 1/243 dilution. PCR was performed using each cDNA sample, calibration sample, Premix Ex Taq™ (manufactured by Takara Bio Inc.), various TaqMan probes (manufactured by Applied Biosystems), and 7500 Real Time PCR System (manufactured by Applied Biosystems). Using mRNA of PPIA (cyclophilin B) as an endogenous control, the expression of PPAR gamma mRNA or FABP4 mRNA was normalized with the PPIA value. Each probe (manufactured by Applied Biosystems) used is shown below.

PPIA: HS99999904
PPAR gamma: HS011155134
FABP4: HS01086177

Figure 5:
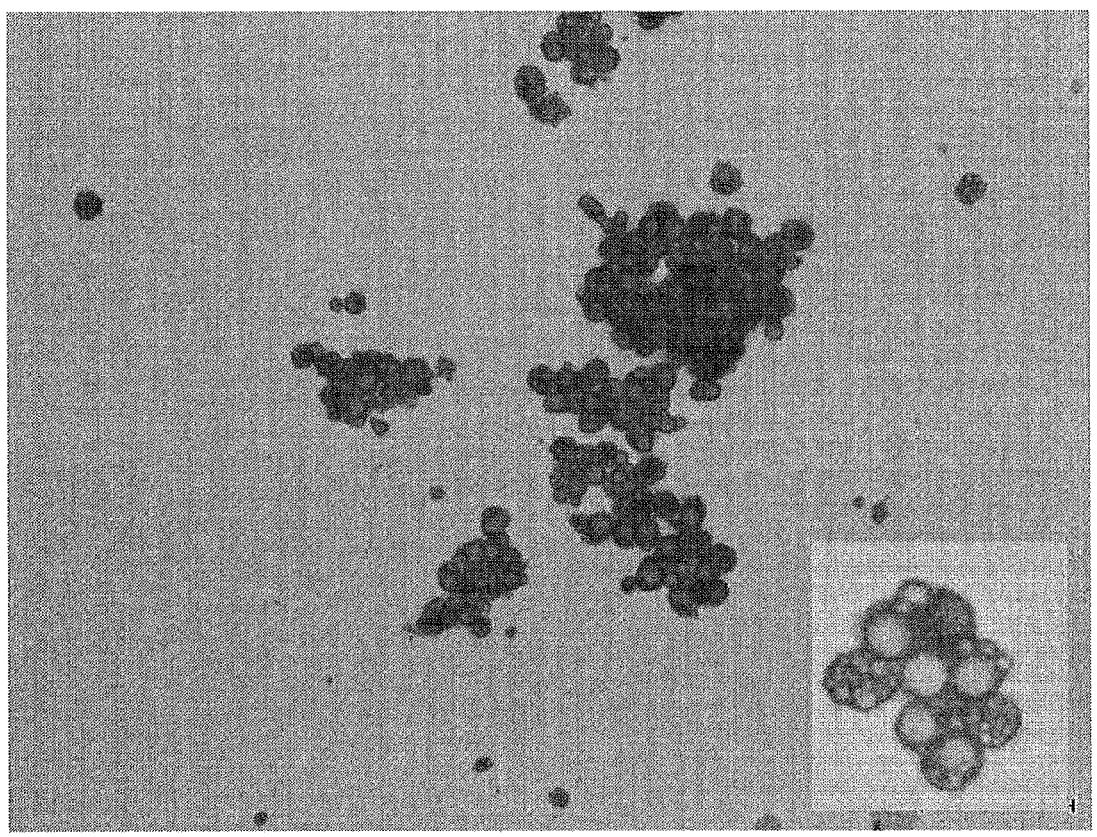
FIG. 5 shows morphology of cells on day 30 from the start of culture.

As a result, when differentiation induction of human fat-derived mesenchymal stem cells into adipocytes was performed to using a human adipocyte differentiation medium composition containing deacylated gellan gum, differentiation into unilocular adipocytes occurred, and the mRNA expression levels of PPAR gamma and FABP4, which are adipocyte markers in the cells, increased. The mRNA expression values of PPAR gamma and FABP4 are shown in Table 5, and cell morphology on day 30 of differentiation induction is shown in FIG. 5.

TABLE 5

| days of culture | PPAR gamma (PPIA normalized value) | FABP4 (PPIA normalized value) |
| --- | --- | --- |
| day 0 | 0.16 | 0 |
| day 10 | 1.88 | 4.39 |
| day 20 | 1.69 | 3.56 |
| day 30 | 2.42 | 6.62 |

Experimental Example 7: Differentiation Induction into Adipocyte by 3D Culture Using Polysaccharides and UCP-1 Expression Diutan gum (KELCO CRETE DG-F, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using the solution, a medium composition was prepared by adding diutan gum at a final concentration of 0.03% (w/v) to a human adipocyte differentiation medium (#CAS11D250, manufactured by TOYOBO). Xanthan gum (manufactured by KELTROL CG, Sansho Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using the solution, a medium composition was prepared by adding xanthan gum at a final concentration of 0.03% (w/v) to a human adipocyte differentiation medium (#CAS11D250, manufactured by TOYOBO). Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. The obtained aqueous solution was sterilized at 121° C. for 20 min in an autoclave. Using the solution, a medium composition was prepared by adding deacylated gellan gum at a final concentration of 0.015% (w/v) to a human adipocyte differentiation medium (#CAS11D250, manufactured by TOYOBO). Successively, as 3D culture method using a low adhesion plate, a human precursor-adipocyte (derived from subcutaneous, #CAS02s05a, manufactured by TOYOBO) was seeded at 90000 cells/mL in the above-mentioned human adipocyte differentiation medium composition added with deacylated gellan gum, xanthan gum or diutan gum, and dispensed to the wells of a 6 well flat bottomed ultralow adhesion surface microplate (manufactured by Corning Incorporated, #3471) at 5 mL per well. The cells were cultured in a static state in a $CO_2$ incubator (37° C., 5% $CO_2$) for 9 consecutive days. The cell suspensions in respective wells were each placed in a 50 mL tube, the evaporated amount of the medium was supplemented with sterile water, human adipocyte differentiation medium composition (5 mL) free of deacylated gellan gum, xanthan gum or diutan gum was added, and the mixture was reseeded in the wells. The cells were continuously cultured in a static state in a $CO_2$ incubator (37° C., 5% $CO_2$) up day 20 from the start of culture, i.e., for 10 days after reseeding. On day 20 from the start of culture, the cell suspension in each well was placed in a 50 mL tube, the evaporated amount of the medium was supplemented with sterile water, human adipocyte differentiation medium composition (5 mL) free of deacylated gellan gum, xanthan gum or diutan gum was added, and the mixture was reseeded in the wells. The cells were cultured in a static state in a CO; incubator (37° C., 5% $CO_2$) up to day 30 from the start of culture, i.e., for 10 days after re-seeding. On day 9, day 20, and day 30 from the start of culture, the cell suspension was recovered from a part of respective wells and each was used for mRNA analysis.

In the mRNA analysis, the total RNA was extracted from the cell suspension also containing the medium using RNeasy Mini kit (manufactured by QIAGEN). Using total RNA and PrimeScript™ RT Master Mix (manufactured by Takara Bio Inc.) and GeneAmp PCR System 9700 (manufactured by Applied Biosystems), a reverse transcription reaction was performed to synthesize cDNA. Each cDNA sample was dispensed, diluted 1/10 with sterile water and used for PCR. As a sample to be used for analytical curve, dispensed and mixed cDNA was used, and a quantification range was set at common ratio 3 and from 1/3 to 1/243 dilution. PCR was performed using each cDNA sample, calibration sample, Premix Ex Taq™ (manufactured by Takara Bio Inc.), various TaqMan probes (manufactured by Applied Biosystems), and 7500 Real Time PCR System (manufactured by Applied Biosystems). Using mRNA of PPIA (cyclophilin B) as an endogenous control, the expression of PPAR gamma mRNA or FABP4 mRNA was normalized with the PPIA value. Each probe (manufactured by Applied Biosystems) used is shown below.

PPIA: HS99999904
PPAR gamma: HS011155134
UCP-1: HS00222453

As a result, when differentiation induction of human precursor-adipocyte into adipocytes was performed using a medium composition containing diutan gum or xanthan gum, which are polysaccharides in the present invention, the mRNA expression level of PPAR gamma, which is an adipocyte marker in the cell, increased to the same level as that of deacylgellan gum. On the other hand, the expression of UCP-1 mRNA which is a beige adipocyte marker and controls heat production further increased in a diutan gum-containing medium and a xanthan gum-containing medium, and showed an effect not less than that of deacylated gellan gum. The mRNA expression values of PPAR gamma and UCP-1 are shown in Table 6 and Table 7.

TABLE 6

| | PPAR gamma (PPIA normalized value) | | |
|---|---|---|---|
| days of culture | deacylgellan gum (0.015%) | xanthan gum (0.03%) | diutan gum (0.03%) |
| day 0 | 0.06 | 0.06 | 0.06 |
| day 9 | 0.95 | 1.12 | 1.02 |
| day 20 | 1.17 | 0.98 | 1.37 |
| day 30 | 1.72 | 1.31 | 1.53 |

TABLE 7

| | UCP-1 (PPIA normalized value) | | |
|---|---|---|---|
| days of culture | deacylgellan gum (0.015%) | xanthan gum (0.03%) | diutan gum (0.03%) |
| day 0 | 0 | 0 | 0 |
| day 9 | 0.35 | 0.30 | 0.29 |
| day 20 | 1.10 | 2.48 | 2.61 |
| day 30 | 1.62 | 3.88 | 4.32 |

(Differentiation Induction into Adipocyte by 3D Culture Using Deacylated Gellan Gum White Adipocyte Formation)

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. The obtained aqueous solution was sterilized at 121° C. for 20 min in an autoclave. Using the solution, a medium composition was prepared by adding deacylated gellan gum at a final concentration of 0.015% (w/v) to a human adipocyte differentiation medium (#CAS1D250, manufactured by TOYOBO). Successively, as 3D culture method using a low adhesion plate, a human precursor-adipocyte (derived from subcutaneous, #CAS02s05a, manufactured by TOYOBO) was seeded at 90000 cells/mL in the above-mentioned human adipocyte differentiation medium composition added with deacylated gellan gum (0.015%), and dispensed to the wells of a 6 well flat bottomed ultralow adhesion surface microplate (manufactured by Corning Incorporated, #3471) at 5 mL per well. The cells were cultured in a static state in a $CO_2$ incubator (37° C., 5% $CO_2$), and cultured for 10 consecutive days. The cell suspensions in respective wells were each placed in a 50 mL tube, the evaporated amount of the medium was supplemented with sterile water, human adipocyte differentiation medium composition (5 mL) free of deacylated gellan gum was added, and the mixture was reseeded in the wells. The cells were cultured in a static state in a $CO_2$ incubator (37° C., 5% $CO_2$), and continuously cultured up to day 20 from the start of culture, i.e., for 10 days after reseeding. On day 20 from the start of culture, the cell suspension in each well was placed in a 50 mL tube, the evaporated amount of the medium was supplemented with sterile water, human adipocyte differentiation medium composition (10 mL) free of deacylated gellan gum was added, and the mixture was re-re-seeded in the wells. The cells were cultured in a static state in a $CO_2$ incubator (37° C., 5% $CO_2$), and cultured up to day 30 from the start of culture, i.e., for 10 days after re-re-seeding.

For the production of white adipocytes, the cell suspension containing the differentiated adipocytes on day 30 was seeded on the top of a 6 well transwell plate (Preset VECELL® 30/6 well(1) HPSVC30-1, Vessel). The differentiation medium that exudes in the lower well part of the transwell through a filter was removed, 10% (v/v) fetal bovine serum (FBS), 1 µg/mL insulin, 2 µM dexamethasone (Takara, Takara-Bio AdipoInducer Reagent) and 1 nM T3 (3,3',5-triiodo-L-thyronine, #T2877, Sigma Ltd. Aldrich) and DMEM medium (manufactured by WAKO) containing 125 nM indomethacin (#I7378, Sigma Ltd. Aldrich), hereinafter (white fat medium) were added to the above-mentioned well to perform medium exchange, and the cells were continuously cultured up to day 59 from the start of culture. The white fat medium in the transwell was exchanged on day 39 and day 50. On day 20, 30, 39, and 59 from the start of culture, the cell suspension was collected from a part of the wells and used for mRNA analysis.

In the mRNA analysis, the total RNA was extracted from the cell suspension also containing the medium using RNeasy Mini kit (manufactured by QIAGEN). Using total RNA and PrimeScript™RT Master Mix (manufactured by Takara Bio Inc.) and GeneAmp PCR System 9700 (manufactured by Applied Biosystems), a reverse transcription reaction was performed to synthesize cDNA. Each cDNA sample was dispensed, diluted ¹⁄₁₀ with sterile water and used for PCR. As a sample to be used for analytical curve, dispensed and mixed cDNA was used, and a quantification range was set at common ratio 3 and from ⅓ to ¹⁄₂₄₃ dilution. PCR was performed using each cDNA sample, calibration sample, Premix Ex Taq™ (manufactured by Takara Bio Inc.), various TaqMan probes (manufactured by Applied Biosystems), and 7500 Real Time PCR System (manufactured by Applied Biosystems). Using mRNA of PPIA (cyclophilin B) as an endogenous control, the expression of PPAR gamma mRNA or FABP4 mRNA was normalized with the PPIA value. Each probe (manufactured by Applied Biosystems) used is shown below.

PPIA: HS99999904
UCP-1: HS00222453
Adiponectin: Hs00605917
Leptin: Hs00174877

As a result, after differentiation into adipocytes with promoted UCP-1 expression using the medium composition of the present invention, followed by exchange with a medium that further promotes white fat formation resulted in an increased expression of Leptin mRNA which is a white adipocyte marker. In contrast, the expression of a beige adipocyte marker UCP-1 conversely decreased. Furthermore, the expression of adiponectin mRNA known as a compact adipocyte marker also decreased as whitening proceeded. It was suggested that culturing in the white fat medium during differentiation induction into adipocytes by the present method results in high expression level of unilocular Leptin mRNA, and growth into white adipocytes. The mRNA expression values of Adiponectin, Leptin and UCP-1 are shown in Table 8.

TABLE 8

| days of culture | UCP-1 (PPIA normalized value) | adiponectin (PPIA normalized value) | Leptin (PPIA normalized value) |
|---|---|---|---|
| day 0 | 0.025 | 0 | 0 |
| day 20 | 259.0 | 133.1 | 0 |
| day 30 | 1414.3 | 155.2 | 0 |
| day 39 | 3.9 | 32.9 | 22.9 |
| day 59 | 0 | 8.2 | 205.7 |

INDUSTRIAL APPLICABILITY

According to the present invention, a unilocular white adipocyte containing one large fat droplet in one cell can be produced in vitro like adipocytes separated from a body. According to the present invention, moreover, a beige-like adipocyte expected to be applicable to not only drug discovery studies but also treatments of diabetes and obesity by transplantation can be produced in vitro.

This application is based on a patent application No. 2017-221360 filed in Japan (filing date: Nov. 16, 2017), the contents of which are incorporated in full herein.

The invention claimed is:

1. A method for producing a unilocular beige adipocyte comprising culturing mesenchymal cells having differentiation potential in a liquid medium composition, thereby inducing differentiation into the unilocular adipocyte, wherein
the liquid medium composition comprises a polymer compound having an anionic functional group that binds via a divalent metal cation to form a structure capable of suspending the mesenchymal cells,
the polymer compound is a polysaccharide,
the mesenchymal cell is a precursor-adipocyte or a mesenchymal stem cell,
the liquid medium composition comprises at least one adipocyte differentiation-inducing factor selected from the group consisting of insulin, glucocorticoid receptor agonist, cAMP phosphodiesterase inhibitor, cyclooxygenase inhibitor, prostaglandin, long chain fatty acid, triiodothyronine, and PPARγ agonist, and
the unilocular adipocyte is UCP-1-positive.

2. The method according to claim 1, wherein the polysaccharide comprises a glucuronic acid moiety.

3. The method according to claim 2, wherein the polysaccharide is deacylated gellan gum, diutan gum, or xanthan gum, or a salt thereof.

4. The method according to claim 3, wherein the polysaccharide is deacylated gellan gum or a salt thereof, and a concentration of the deacylated gellan gum or a salt thereof in the medium composition is 0.01 to 0.05% (w/v).

5. The method according to claim 3, wherein the polysaccharide is diutan gum or xanthan gum or a salt thereof, and a concentration of the diutan gum or xanthan gum or a salt thereof in the medium composition is 0.01 to 0.5% (w/v).

6. The method according to claim 1, wherein the adipocyte differentiation-inducing factor contains insulin, a glucocorticoid receptor agonist, and a cyclooxygenase inhibitor.

7. The method according to claim 6, wherein the glucocorticoid receptor agonist is dexamethasone.

8. The method according to claim 1, wherein the adipocyte differentiation-inducing factor contains insulin, a glucocorticoid receptor agonist, and a cAMP phosphodiesterase inhibitor.

9. The method according to claim 8, wherein the glucocorticoid receptor agonist is dexamethasone.

10. The method according to claim 1, further comprising lowering a concentration of the polymer compound in the liquid medium composition comprising the suspended mesenchymal cells to a concentration incapable of suspending the mesenchymal cells, thereby allowing the mesenchymal cells to become unsuspended and the unilocular adipocytes to maintain a floating state, and collecting unilocular adipocytes that maintain the floating state.

* * * * *